(12) United States Patent
Ugander et al.

(10) Patent No.: US 12,426,822 B2
(45) Date of Patent: Sep. 30, 2025

(54) METHOD AND A SYSTEM FOR PRODUCING A STANDARD 12-LEAD ECG

(71) Applicant: KOZOR UGANDER CAPITAL PTY LIMITED, Sydney (AU)

(72) Inventors: Martin Ugander, Cremorne (AU); Teddy Curtis, London (GB)

(73) Assignee: KOZOR UGANDER CAPITAL PTY LIMITED, Sydney (AU)

( * ) Notice: Subject to any disclaimer, the term of this patent is extended or adjusted under 35 U.S.C. 154(b) by 436 days.

(21) Appl. No.: 18/246,901

(22) PCT Filed: Sep. 24, 2021

(86) PCT No.: PCT/EP2021/076338
§ 371 (c)(1),
(2) Date: Mar. 28, 2023

(87) PCT Pub. No.: WO2022/063975
PCT Pub. Date: Mar. 31, 2022

(65) Prior Publication Data
US 2023/0363684 A1    Nov. 16, 2023

(30) Foreign Application Priority Data
Sep. 28, 2020  (EP) .................................... 20198752

(51) Int. Cl.
*A61B 5/00*        (2006.01)
*A61B 5/282*       (2021.01)

(52) U.S. Cl.
CPC ............ *A61B 5/282* (2021.01); *A61B 5/6823* (2013.01); *A61B 5/6824* (2013.01)

(58) Field of Classification Search
CPC ..... A61B 5/282; A61B 5/6823; A61B 5/6824; A61B 5/0006; A61B 5/0022; A61B 5/327; A61B 5/332; A61B 5/681; A61B 5/341; A61B 5/318
See application file for complete search history.

(56) References Cited

U.S. PATENT DOCUMENTS

2024/0423527 A1*  12/2024  Kwon ................... A61B 5/6801
2025/0000421 A1*   1/2025  Kwon .................... A61B 5/319

* cited by examiner

*Primary Examiner* — Scott M. Getzow
(74) *Attorney, Agent, or Firm* — Vorys, Sater, Seymour and Pease LLP; Khaled Shami

(57) ABSTRACT

A method and a system are disclosed for producing a standard 12-lead ECG formed by three standard limb leads I, II, III, three standard augmented limb leads aVR, aVL, aVF, and six standard precordial leads V1 to V6, from fifteen asynchronous leads, sequentially acquired by a single-lead electronic device having two electrodes only. The sequentially acquired leads include three acquired limb leads I, II, and III, and twelve acquired arm-referenced chest leads CR1-CR6 and CL1-CL6. Each pair of acquired leads CRi and CLi of acquired leads CR1-CR6 and CL1-CL6 represent voltage differences acquired between a right arm and a left arm, respectively, and a common chest position Ci associated with a corresponding standard precordial lead Vi.

16 Claims, 16 Drawing Sheets

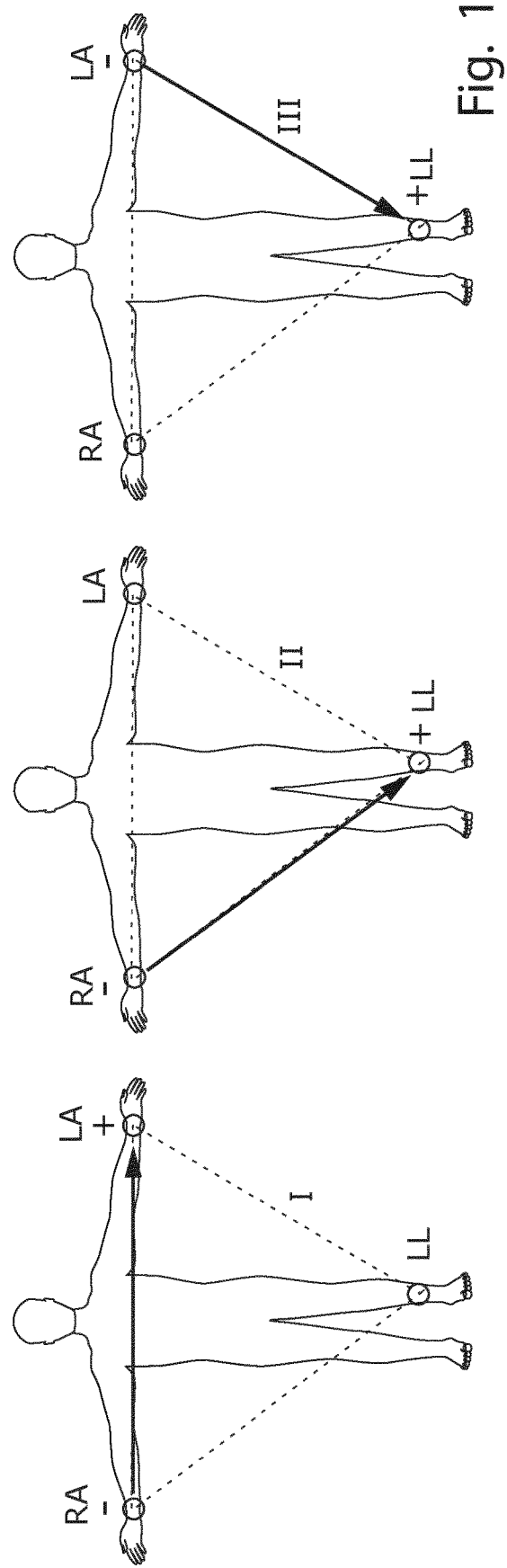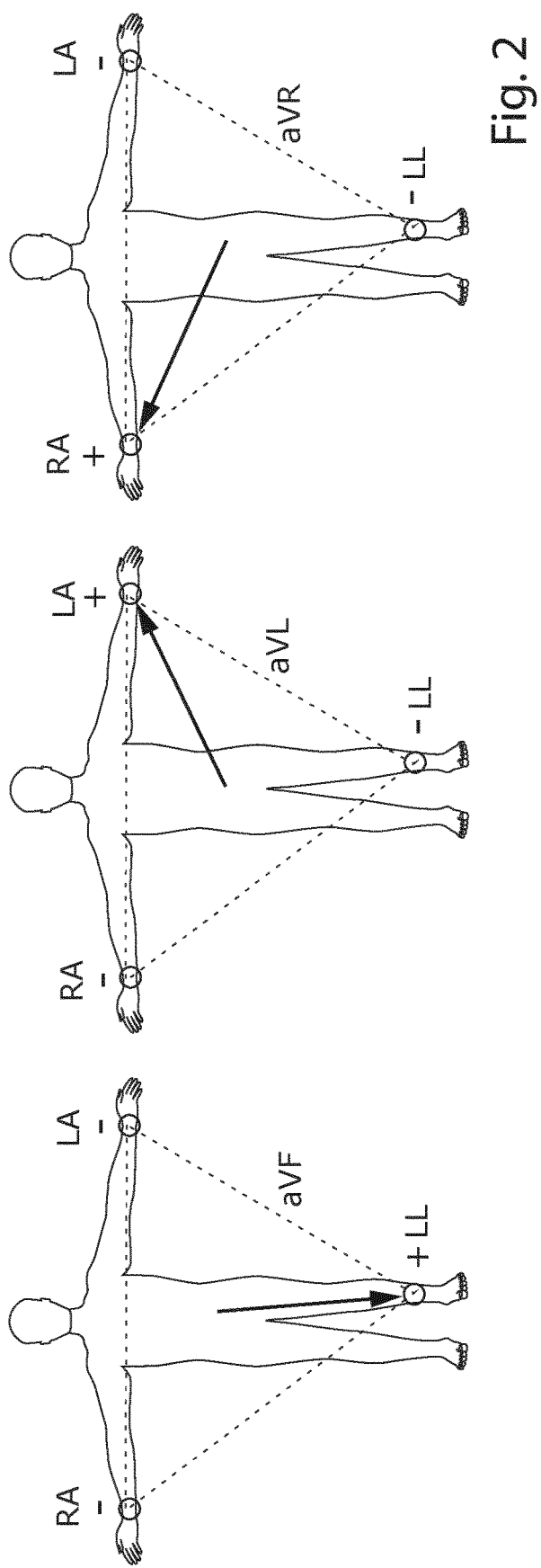

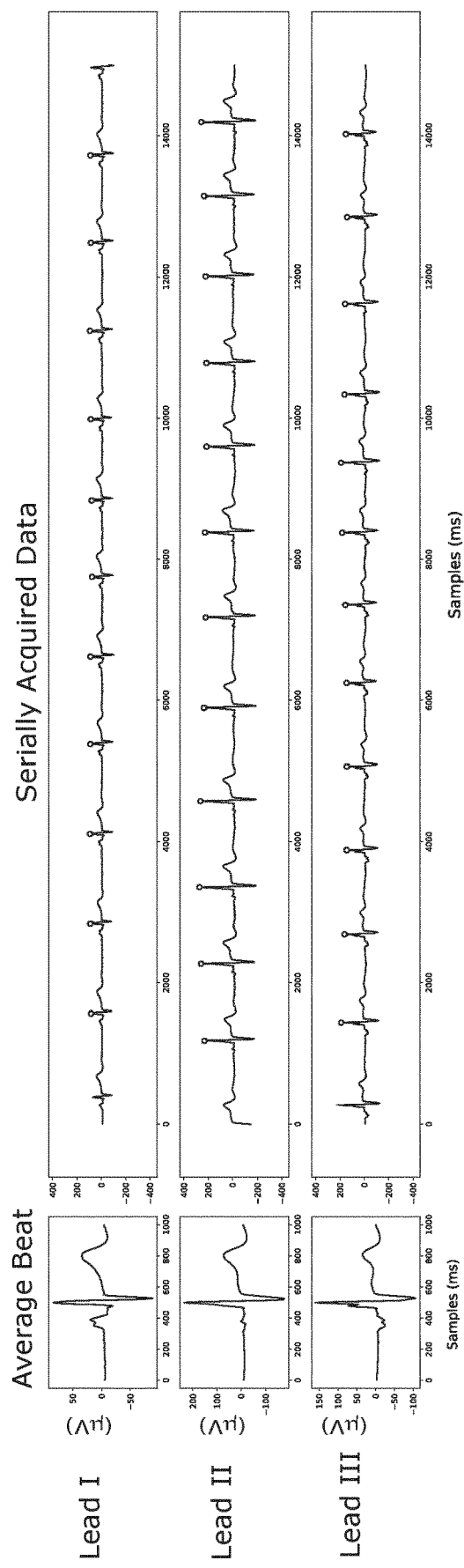

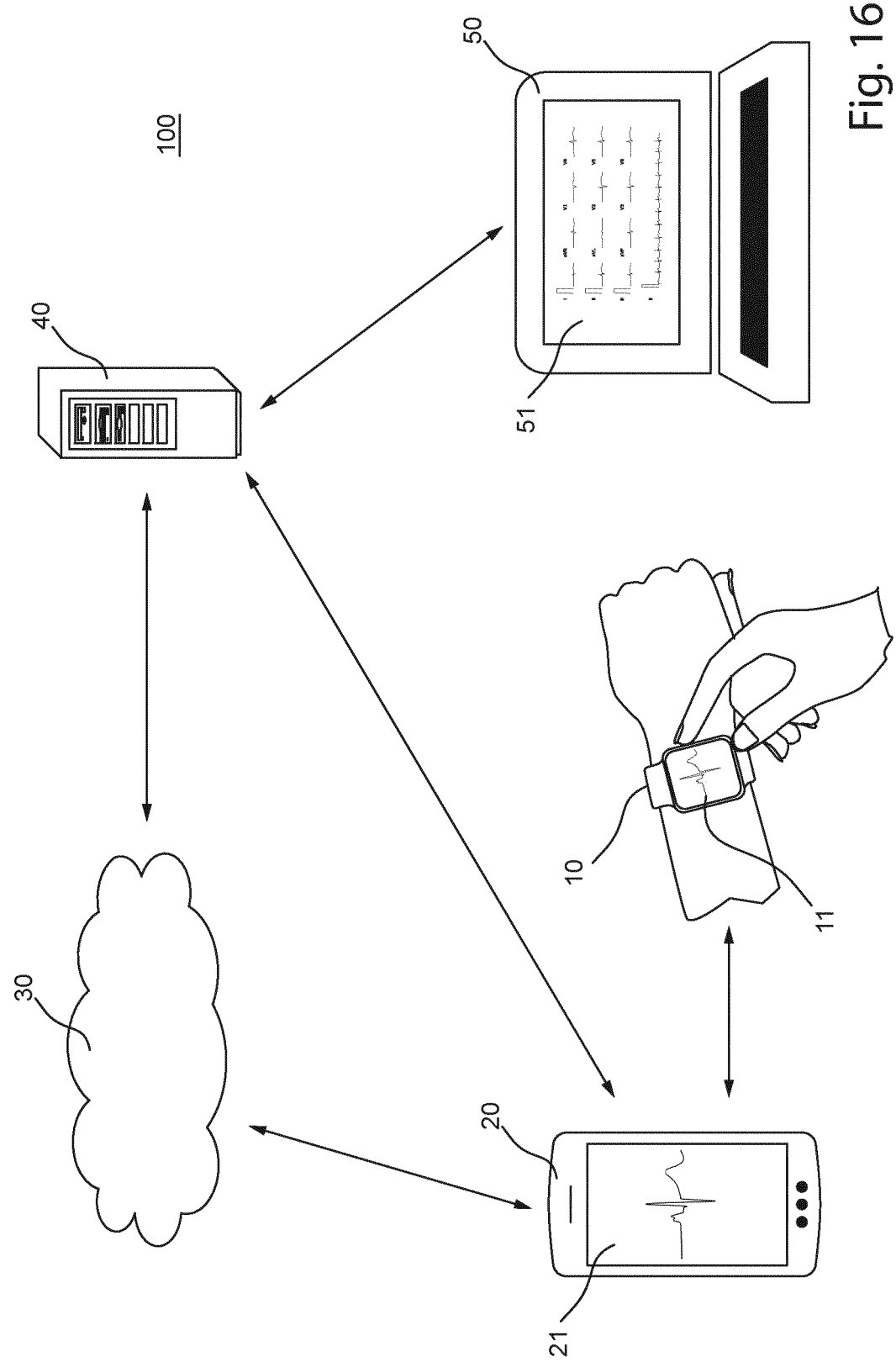

METHOD AND A SYSTEM FOR PRODUCING A STANDARD 12-LEAD ECG

TECHNICAL FIELD

The present inventive concept relates to producing a standard 12-lead electrocardiogram, ECG. More specifically, the present inventive concept relates a method and a system using sequentially acquired leads for producing a standard 12-lead ECG.

BACKGROUND

The electrical activity of the heart can be measured as the voltage over time between two electrodes positioned on the surface of the body. The waveform of voltage over time from two electrodes is referred to as a lead. In the ECG literature, the term "lead" is sometimes incorrectly used also for the electrodes or the wires, but the correct meaning of the term "lead" is the actual voltage waveform over time as measured between two electrodes. The term "lead" is also used for leads calculated from the measured or acquired leads.

In Paul Kligfield, et al, "Recommendations for the Standardization and Interpretation of the Electrocardiogram", pp. 1306-1324, Mar. 13, 2007, the American Heart Association (AHA), et al, present a statement relating to a standardization for 12-lead ECGs. In the present disclosure, the standard proposed in this document will be referred to as the "AHA Standard". As used in the present disclosure, the term "standard 12-lead ECG" is to be construed as a 12-lead ECG according to the AHA Standard. As used herein, the term "twelve standard leads" is to be construed as the twelve leads of a standard 12-lead ECG.

A standard 12-lead ECG is comprised of twelve standard leads, including: three limb leads (I, II, and III), three augmented limb leads (aVR, aVL, and aVF), and the six precordial leads (V1, V2, V3, V4, V5, and V6).

In modern electrocardiographs, also referred to as ECG machines, a standard 12-lead ECG is conventionally created or produced using ten electrodes connected to the electrocardiograph and placed at predefined positions on the body surface. Four of the ten electrodes are placed on the four limbs. Six of the ten electrodes are placed on the chest over the heart, at predefined or standard chest electrode positions. The electrical signals simultaneously acquired by the ten electrodes are amplified and processed (including calculating certain leads) to generate twelve channels of ECG data. The resulting twelve channels or leads are generally referred to as, on the one hand, the six limb leads that represent the electrical activity in the frontal plane (I, II, III, aVR, aVL, aVF), and on the other hand the six precordial leads that represent the electrical activity approximately corresponding to the horizontal plane (V1, V2, V3, V4, V5, V6).

Leads initially recorded or acquired by a conventional 12-lead electrocardiograph are thus simultaneously measured using ten electrodes attached to the machine via ten cables, using different combinations of simultaneous measurements between ten standard electrode positions on the body: right arm (RA), left arm (LA), left leg (LL), and right leg (RL), and chest 1 through chest 6 (C1-C6). The terms RA, LA, LL, RL, and C1-C6 may refer to the electrode positions as well as the actual ten electrodes. These ten standard electrode positions form part of the AHA standard. In the present disclosure, the limb electrode positions RA, LA, LL, RL may refer to any position on the respective limb, not necessarily on the wrists and on the ankle. FIG. 1 illustrates that the three limb electrodes RA, LA, and LL form a triangle (Einthoven's Triangle). The electrode at RL on the right leg is used as a ground electrode, and effectively does not contribute to any lead. FIG. 3 illustrates the six predefined chest electrode positions C1-C6.

In a standard 12-lead ECG machine, all ten electrodes are normally connected by wires to the machine, and the leads are all measured simultaneously. Thereby, the heart's electrical potential can be measured simultaneously from twelve different angles and recorded over a period of time (usually 10 seconds or more), wherein each angle corresponds to one of the 12 standard leads, respectively. Accordingly, the simultaneously measured leads obtained by a modern ECG machine will by definition all be mutually time-aligned or "synchronous". This is of relevance since the three augmented limb leads aVR, aVL, aVF, and the six precordial leads V1-V6, which all form part of the standard 12-lead ECG, are continuously calculated from the measured leads during the acquisition.

During recent years, portable or wearable single-lead electronic devices of various types and designs have been developed using two electrodes only, wherein typically one lead only (limb lead I) is measured and recorded. Some of these prior-art electronic devices are in the form of smartwatches, smartphones, or the like, while others are in the form of or dedicated single-lead ECG devices. The two electrodes may be integrated in such a single-lead device, or they may be connected by wire or wirelessly to the electronic device. Although such single-lead ECG devices may be used for monitoring and detecting certain conditions, e.g. arrhythmia, single-lead ECG devices producing one single lead only have a limited use for cardiac diagnostics.

There exist several prior-art single-lead smartwatch-based ECG devices from different manufacturers, including the Apple Watch Series 4, 5, and 6® (Apple Inc, Cupertino, CA, USA) with two integrated electrodes allowing a single-lead ECG to be recorded, typically limb lead I. Using the Apple Watch, for example, the limb lead I may be measured by recording the voltage difference over time between for instance the right index finger contacting the crown of watch, and the left arm wrist contacting the rear side of the watch, corresponding to Einthoven's limb lead I. ECG recording may be activated by the patient/user, and thereafter a pdf document of the single-lead ECG may be produced using an associated application (app), for subsequent printing and/or forwarding for diagnostic assessment.

During recent years, multiple attempts have been made to use single-lead ECG devices also for generating various types of multiple-lead ECGs. Especially, extensive efforts have been made to reproduce or "synthesize" the standard 12-lead ECG, similar to a synchronously recorded standard 12-lead ECG, but using a single-lead ECG device with two electrodes only and sequential lead acquisition, producing asynchronous acquired leads. So far, such efforts have been unsuccessful, and only other types of multiple-lead ECG have been produced, which are different from the standard 12-lead ECG and which are not suitable for most diagnostic uses.

An article by Alexander Samol, Kristina Bischof, Blerim Luani, Dan Pascut, Marcus Wiemer and Sven Kaese, "Single-Lead ECG Recordings Including Einthoven and Wilson Leads by a Smartwatch: A New Era of Patient Directed Early ECG Differential Diagnosis of Cardiac Diseases?", Sensors 2019, 19, 4377, discloses the results of using an Apple Watch for sequentially acquiring multiple leads. The method proposed in that study does not produce a standard 12-lead ECG. In particular, the six standard precordial leads V1-V6 were not produced. Instead, non-standard precordial leads were recorded by—simultaneously—holding one hand over the wrist of the other hand, holding both hands and forearms in contact with the chest, and holding the watch in sequence at the three chest electrode positions C1, C4, and C6, thereby recording three leads referred to as "Wilson-like" chest leads in the article. These three non-standard leads are not the same as the six standard precordial leads V1-V6, and cannot be used for producing a standard 12-lead ECG for reliable diagnostics.

Another example of prior-art single-lead ECG devices is the smartwatches available from AliveCor, Inc (US). Patents describing the representative technology include U.S. Pat. No. 9,986,925 B2 and U.S. Pat. No. 9,833,158 B2.

Drawbacks and unsuccessful results of prior-art attempts to use single-lead ECG devices for creating multiple-lead ECGs are also discussed in Kahkashan Afrin, Parikshit Verma, Sanjay S. Srivatsa, and Satish T. S. Bukkapatnam, "Simultaneous 12-lead Electrocardiogram Synthesis using a Single-Lead ECG Signal: Application to Handheld ECG Devices", 20 Nov. 2018. As mentioned in that article, many attempts have been made to derive or "synthesize" a standard 12-lead ECG from single-lead portable devices by sequentially recording signals from a single-lead (dual-electrode) device, one acquisition or lead at a time. Results obtained by the smartwatch from AliveCor®, Inc are described as follows in that article: "Vectorcardiography (VCG) analysis suggests that the cardiac axis synthesized from these earlier attempts deviates considerably from that estimated from 12-lead and/or Frank lead measurements." Accordingly, by using VCG analysis, it has been demonstrated that prior attempts, such as those used by AliveCor®, produce ECGs that deviate significantly from a synchronous standard 12-lead ECG and, therefore, are unsatisfactory from a clinical standpoint. Further, a different proposed method presented in that article has the drawback that it requires an initial recording of a simultaneous standard synchronous 12-lead ECG using a conventional 12-lead ECG machine. Also, the previously acquired and simultaneously recorded standard 12-lead ECG has to be uploaded to a cloud-based server for the proposed method to operate. When a single-lead ECG is subsequently recorded, the previously acquired "true" standard 12-lead ECG is used for synthesizing the missing 11 lead signals at that time.

Accordingly, there is a need to produce or "synthesize" a standard 12-lead ECG, formed by the 12 standard ECG leads, from sequentially acquired leads using a single-lead ECG device, such as by using a portable or wearable single-lead electronic device, and without the need to record any standard synchronous 12-lead ECG.

SUMMARY OF INVENTION

In the light of the above, it is an object of the present inventive concept to provide a method and a system wherein the above-mentioned disadvantages of the prior art are addressed.

According to a first aspect of the inventive concept, there is provided a method for producing a standard 12-lead ECG formed by three standard limb leads I, II, III, three standard augmented limb leads aVR, aVL, aVF, and six standard precordial leads V1 to V6, from fifteen asynchronous, sequentially acquired leads, including three acquired limb leads I, II, and III, termed acquired leads I-III, and twelve acquired arm-referenced chest leads CR1-CR6 and CL1-CL6, termed acquired leads CR1-CR6 and CL1-CL6;

wherein, for integer i equal from 1 to 6, each pair of acquired leads CRi and CLi of acquired leads CR1-CR6 and CL1-CL6 represent voltage differences acquired between a right arm and a left arm, respectively, and a common chest position Ci associated with a corresponding standard precordial lead Vi, said method comprising:

creating time-aligned limb leads I, II and III, termed time-aligned leads I-III, from acquired leads I-III, by using the formula lead II–lead I=lead III;

calculating three time-aligned augmented limb leads aVR, aVL, and aVF from time-aligned leads I-III;

performing, for integer i equal from 1 to 6, one of (a) and (b):
  (a) creating a time-aligned arm-referenced chest lead CRi, termed time-aligned CRi, by time-aligning acquired lead CRi with acquired lead I such that a calculated difference CRi–I, representing a calculated arm-referenced chest lead CLi, termed calculated lead CLi, has an optimal agreement with acquired lead CLi,
  (b) creating a time-aligned acquired arm-referenced chest lead CLi, termed time-aligned CLi, by time-aligning acquired lead CLi with acquired lead I such that a calculated sum CLi+I, representing a calculated arm-referenced chest lead CRi, termed calculated lead CRi, has an optimal agreement with acquired lead CRi;

and calculating, for integer i equal from 1 to 6, a time-aligned precordial lead Vi from time-aligned lead I, one of time-aligned lead II and time-aligned lead III, and one of time-aligned lead CRi and time-aligned lead CLi, for forming time-aligned precordial leads V1-V6;

wherein time-aligned leads I-III, time-aligned augmented leads limb leads aVR, aVL, and aVF, and time-aligned precordial leads V1-V6 together form a standard 12-lead ECG.

The inventive concept makes it possible to produce a standard 12-lead ECG, including the twelve standard leads (especially including the six standard precordial leads V1-V6) from sequentially acquired leads. Especially, the inventive concept makes it possible to produce—with an exceptional high degree of accuracy—all twelve standard leads I, II, III, aVR, aVL, aVF, and V1-V6 of a standard 12-lead ECG from a plurality of sequentially acquired, or "asynchronous" ECG signals. In its broadest aspect, the method according to the inventive concept includes actions performed on the fifteen specified asynchronous acquired leads at hand for producing a standard 12-lead ECG. According to some embodiments, the method according the inventive concept also includes the act or acts of sequentially acquiring or recording the leads.

The inventive concept makes it possible to produce a standard 12-lead ECG, including all twelve standard leads using a single-lead electronic device having two electrodes only, and sequentially changing positions of the two electrodes on the body of a subject during a sequential acquisition of fifteen leads. Such a single-lead (two-electrode) electronic device may especially be a portable or wearable electronic device, such as a smartwatch, a smartphone, a tablet, or a dedicated electronic ECG device. The two electrodes may be integrated in the electronic device, such as integrated in a smartwatch. One or both electrodes may also be electrodes connected by wire or wirelessly to the electronic device.

A specific advantage obtained by the inventive concept over the prior-art discussed above relates to the precordial leads V1-V6. When recording a conventional synchronous 12-lead ECG using an ECG machine with ten electrodes, the precordial leads are continuously "calculated" during the ECG recording by subtracting the potential at the so-called Wilson central terminal (WCT) from the potential at each chest electrode C1-C6. As mentioned in the AHA standard, the WCT is the average potential of the three limb potentials, RA, LA, and LL. In the prior-art attempt of using single-lead devices, the right arm, the left arm have been used as reference instead of the WCT. The measured PQRST waveforms of measured CR leads and CL leads are not identical to those of the corresponding calculated precordial leads recorded with the WCT reference. Since the inventive concept produces the true precordial leads V1-V6, a true standard 12-lead ECG may be produced from sequentially acquired leads.

It is thus an insight of the present inventive concept that is possible to create especially the six standard precordial leads V1-V6 from sequentially acquired leads, by sequentially acquiring fifteen specific leads and by performing time-alignment and calculations on the fifteen sequentially acquired leads. This is a substantial insight considering that the standard precordial leads are defined as $Vi=Ci-WCT$, where $WCT=\frac{1}{3}(RA+LA+LL)$. It is not possible to place a single electrode at the WCT since it represents a "virtual" electrode that is calculated from RA, LA and LL. In conventional 10-electrode ECG machines, WCT can be continuously calculated during the synchronous recording, by averaging the three simultaneous measurements from electrodes RA, LA and LL to continuously give an average potential of the body.

The nine standard leads aVR, aVL, aVF, and V1, V2, V3, V4, V5, and V6 are defined as the voltage between a given physical electrode and a virtual electrode calculated from simultaneous measurement from a combination of physical electrodes. It is an insight of the present inventive concept that in order to correctly measure aVR, aVL, aVF, V1, V2, V3, V4, V5, and V6, one must very accurately time-align all sequentially acquired signals in order to perform correct calculations based on acquired leads.

It is also an insight of the present inventive concept that it is possible to create twelve time-aligned standard leads of a standard 12-lead ECG by performing the inventive method on fifteen specific and sequentially acquired leads, that is three more leads than the number of leads in the standard ECG, and it is substantially more acquired leads than the number of acquired leads in a conventional 10-electrode electrocardiograph with simultaneous acquisition. As a comparison, many of today's digital 10-electrode electrocardiographs record only eight channels of independent information simultaneously, with four of the limb leads being derived from the other two as will be described in detail below. By performing the inventive method on fifteen specific asynchronous, sequentially acquired leads, specific redundant information in the acquired leads is available making it possible to produce the twelve standard leads.

Accordingly, the inventive concept and its solution to how it is possible, using two electrodes only with sequential measurements, to reproduce a correct standard 12-lead ECG, and especially including the standard precordial leads V1-V6 and not any directly measured "quasi chest leads" as a substitute for the standard precordial leads V1-V6, includes the insight that by using certain acquired leads that do not form part of the group of the twelve "standard leads", including certain redundant information, and performing time-alignments and calculations based on these non-standard leads in combination with acquired standard limb leads I-III, it is possible to perform all time-alignment and calculations required for obtaining all twelve standard leads producing a standard 12-lead ECG.

It is also an insight of the present invention that the six time-aligned standard precordial leads V1-V6 may be created by performing the inventive method on fifteen sequentially acquired leads comprising especially both the six arm-referenced chest leads CR1-CR6, and the six arm-referenced chest leads CL1-C6.

Definitions

As used herein, the term "lead" will be used both for initially acquired leads measured as potential differences over time between pairs of electrodes on the body surface, and for subsequently time-aligned, averaged or calculated leads, especially including all of the twelve standard leads forming a standard 12-lead ECG. Where appropriate for clarification, the terms "acquired", "time-aligned", "averaged", and "calculated" will be used to designate the "state" of the different leads.

As used herein, the term "Standard 12-lead ECG" is to be interpreted as a 12-lead ECG as described in the background section above, i.e. including the twelve standard leads I, II, III, aVR, aVL, aVF, and V1-V6. Especially, the expressions "Standard 12-lead ECG" and "the twelve standard leads" should be interpreted as not encompassing precordial quasi-leads, or any arm-referenced chest leads, not representing the standard precordial leads V1 to V6.

As used herein, the term "single-lead ECG device" or similar terms is to be interpreted as a device configured to measure or record only one lead at a time in sequence (asynchronous measurement), in contrast to ECG devices or machines configured to generate all twelve standard leads simultaneously using ten electrodes. Accordingly, the term "single-lead ECG device" is used also to comprise existing single-lead ECG devices if modified by hardware and/or software to be used in implementing the inventive concept of generating all of the twelve standard ECG leads of a standard 12-lead ECG, but still by recording one lead at a time in sequence.

In the inventive concept, only two electrodes have to be used. These may be placed at the same electrode positions as in a conventional 12-lead ECG. Therefore, in the present application, the terms RA, LA, and LL, and C1-C6 will be used as referring to the respective electrode positions, rather than the electrodes as such.

As used herein, the terms "sequential acquisition", "sequential recording", "sequential measurement", and the like should be interpreted as the act of recording or acquiring the respective electrical ECG signals in sequence over time, one after the other, using different pairs of electrode positions on the body between each measurement, and resulting in asynchronous acquired leads.

As used herein, the term "electrode" means a discrete electrode, or an electrode assembly, configured to measure the potential at a given position on the body surface. Accordingly, also an electrode assembly formed by two or more electrode parts or portions is considered as an "electrode".

As used herein, the term "calculating" means computing, using one or more electronic processing units for calculating or computing.

The acts of creating the time-aligned leads in the method according to the inventive concept may comprise averaging each acquired lead of the fifteen acquired leads for creating fifteen corresponding averaged beat waveforms, and using the averaged beat waveforms as the acquired leads in the step of creating time-aligned leads I-III, and in step (a) and (b) of creating time-aligned leads CR1-CR6, and time-aligned leads CL1-CL6, respectively. Such averaged beat waveforms are sometimes also referred to as "averaged complexes" in the literature. Obviously, such averaging requires that each acquired lead is recorded over a time period representing more than one heartbeat. The averaging of each lead may be performed by detecting the maximal deflection of each QRS complex in the lead, and using this maximal deflection to align the beats and to form an averaged beat therefrom, as well as incorporating various strategies for excluding arrhythmic or extra beats of a different waveform morphology from this averaging.

In some embodiments including such averaging of the acquired ECG signals to form averaged beat waveforms, the method may include the following:

time-aligned leads I-III are created from averaged beat waveforms I-III, and will be in the form of time-aligned average beat waveforms I-Ill;

time-aligned augmented limb leads aVR, aVL, and aVF are calculated from time-aligned leads I-III, and will be in the form of time-aligned average beat waveforms;

in step (a) and step (b), each one of acquired arm-referenced leads CRi and CLi, respectively, is averaged for forming an associated averaged beat waveform CRi and CLi, respectively, and the associated averaged beat waveforms CRi and CLi are used for performing the time-aligning in step (a) and step (b), wherein resulting time-aligned leads CR1-CR6 and CL1-CL6 will be in the form of time-aligned average beat waveforms; and the standard precordial leads V1-V6 are calculated from the above time-aligned average beat waveforms, and the calculated V1-V6 will also be in the form of time-aligned average beat waveforms.

In some embodiments including such averaging of the acquired ECG signals to form average beat waveforms, the initially acquired raw data may be dismissed with after averaging. However, it may be preferred to save all or at least some of the sequentially acquired raw data. It may be used for quality control. It may also be used by a healthcare professional or algorithm for evaluating the cardiac rhythm. For some cardiac arrhythmia conditions, the morphology of the beat waveform is not decisive but rather the rhythm of the waveform over time.

According to an embodiment, the time-aligning in step (a) is performed by iteratively shifting acquired lead CRi and acquired lead I in relation to each other to achieve said optimal agreement between said difference CRi–I and acquired lead CLi; and the time-aligning in step (b) is performed by iteratively shifting acquired lead CLi and acquired lead I in relation to each other to achieve said optimal agreement between said sum CLi+I and acquired lead CRi.

According to an embodiment, the act of creating time-aligned leads I-III from acquired leads I-III comprises time-aligning a first acquired lead of acquired leads I-III with a second acquired lead of acquired leads I-III using a third acquired lead of acquired leads I-III as reference. As a non-limiting example, acquired lead II may be time-aligned with acquired lead I, using acquired lead III as reference. The time-alignment may be performed such that a calculated difference II-I, representing a calculated lead III, has an optimal agreement with acquired lead III. The calculated lead III may be used as time-aligned lead III. In some embodiments, the time-alignment may be performed by iteratively shifting said first acquired lead and second acquired lead in relation to each other to achieve said optimal agreement. In other embodiments, acquired leads II and III, or acquired leads I and III, are used as said first and second acquired leads for time-alignment.

The various acts or steps of the method according to the inventive concept may be performed in an arbitrary order, still resulting in the twelve standard leads together forming standard 12-lead ECG.

According to some embodiments, time-aligned lead I may be created before performing step (a) or step (b), respectively. Time-alignment in step (a) or (b), respectively, may subsequently be performed using time-aligned lead I. As an alternative, it is also possible to start by time-aligning all or some of acquired arm-referenced chest leads with acquired lead I, and subsequently perform the act of creating time-aligned leads I-Ill. These and other possible variants will be discussed further below.

With respect to the order of the acts or steps of the method according to the inventive concept, it may also be noted that the calculation of the six time-aligned precordial leads V1-V6 may be performed as a final step when all time-aligned leads are available, or alternatively the calculation may be performed for each precordial lead Vi as soon as the time-aligned leads required for calculating that specific precordial lead Vi are available.

Step (a) and step (b) of the method according to the inventive method are alternatives to each other for each integer i equal from 1 to 6, since either time-aligned lead CRi or time-aligned lead CLi may be used in the calculation of the associated time-aligned standard precordial lead Vi. In some embodiments, step (a) only is used for creating the six time-aligned arm-referenced chest leads CR1-CR6, while step (b) is not used and the six time-aligned arm-referenced chest leads CL1-CL6 are not created. In some embodiments, step (b) only is used for creating the six time-aligned arm-referenced chest leads CL1-CL6, while step (a) is not used and the six time-aligned arm-referenced chest leads CR1-CR6 are not created. Combinations of these embodiments are also possible, and in some embodiments both steps (a) and (b) are performed for each i equal from 1 to 6.

In some implementations, the acquisition of the twelve arm-referenced chest leads CR1-CR6 and CL1-CL6 may be performed in pairs: For integer i equal from 1 to 6, acquired lead CRi and acquired CLi are measured sequentially, one directly after the other in any order, while keeping one electrode positioned at an associated common chest position Ci, thus measuring each pair of leads CRi CLi in any order directly after each other without moving the chest electrode between the two measurements.

The redundancy of information present in the fifteen acquired leads may be used for obtaining additional advantages, including noise reduction and/or reduced acquisition time. Such embodiments may comprise averaging each time-aligned lead with an associated calculated version of the same lead, for creating an associated averaged time-aligned lead, thereby utilizing the available redundant information as much as possible. Details and examples of such averaging technique will be given in the detailed description below.

According to an embodiment, the method according to the inventive method may further comprise creating a vectorcardiogram, VCG, by mathematically deriving the so-called Frank leads X, Y, and Z from time-aligned leads I and II, and time-aligned precordial leads V1-V6.

An important method in the assessment of an ECG can be evaluation of the VCG. The VCG involves acquiring leads X, Y, and Z according to Frank, and these leads represent the three orthogonal spatial directions of the body (left-right, up-down, front-back). Acquisition of the Frank leads X, Y, and Z is rarely performed, but the Frank leads X, Y and Z can be derived mathematically from the standard 12-lead ECG, more specifically from standard limb leads I and II, and standard precordial leads V1-V6. Further information may be found in Kors J A, van Herpen G, Sittig A C, van Bemmel J H., "Reconstruction of the Frank vectorcardiogram from standard electrocardiographic leads: diagnostic comparison of different methods." Eur Heart J. 1990 December; 11(12):1083-92.

It has been shown in that study that the derived VCG has a very good agreement with the Frank X, Y and Z leads. The derivation was developed using regression analysis to determine the optimal coefficients to multiply limb leads I, II, and precordial leads V1-V6 by in order to derive leads X, Y, and Z. As an example, Frank lead X may be calculated as follows using a reconstruction matrix according to Kors:

$$X=0.38I-0.07II-0.13V1+0.05V2-0.01V3+0.14V4+0.06V5+0.54V6$$

When creating Frank leads according to this embodiment of the invention, the eight standard leads (I, II, V1-V6) used in the above calculation are all time-aligned as result of being created by the inventive method, and can therefore be used for mathematically deriving Frank leads X, Y, and Z for producing a correct VCG. VCG analysis also requires simultaneous accuracy of time-alignment for the entire 12-lead ECG.

The VCG obtained by this embodiment may be optionally used for clinical diagnosis by an algorithm or a healthcare professional visually inspecting the VCG or numerical measures derived from the VCG. However, the obtained VCG may, in the form of the derived Frank leads X, Y, and Z, advantageously also be used for evaluation by advanced diagnostic algorithms, since it has been demonstrated that the Frank leads are especially advantageous to use for such diagnostic algorithms. Furthermore, a VCG plot derived by the inventive concept may be used to clearly demonstrate the high degree of agreement with a simultaneously recorded standard 12-lead ECG, as will be demonstrated below.

According to a second aspect of the inventive concept, there is provided a system for producing a standard 12-lead ECG formed by three standard limb leads I, II, III, three standard augmented limb leads aVR, aVL, aVF, and six standard precordial leads V1 to V6, the system comprising:
  two electrodes;
  at least one processing unit configured to perform the acts of:
    sequentially acquiring fifteen ECG leads between the two electrodes, while the two electrodes are sequentially moved to different positions on a subject's body, including three acquired limb leads I, II, and III, termed acquired leads I-III, and twelve acquired arm-referenced chest leads CR1-CR6 and CL1-CL6, termed acquired leads CR1-CR6 and CL1-CL6, wherein, for integer i equal from 1 to 6, each pair of acquired leads CRi and CLi of acquired leads CR1-CR6 and CL1-CL6 represent voltage differences acquired between a right arm and a left arm, respectively, and a common chest position Ci associated with a corresponding standard precordial lead Vi;
    creating three time-aligned limb leads I, II and III, termed time-aligned leads I-III, from acquired leads I-III, by using the formula lead II−lead I=lead III;
    calculating three time-aligned augmented limb leads aVR, aVL, and aVF from time-aligned leads I-Ill;
    for integer i equal from 1 to 6,
      (a) creating a time-aligned arm-referenced chest lead CRi, termed time-aligned CRi, by time-aligning acquired lead CRi with acquired lead I such that a calculated difference CRi−I, representing a calculated arm-referenced chest lead CLi, has an optimal agreement with acquired lead CLi, or
      (b) creating a time-aligned acquired arm-referenced chest lead CLi, termed time-aligned CLi, by time-aligning acquired lead CLi with acquired lead I such that a calculated sum CLi+I, representing a calculated arm-referenced chest lead CRi, has an optimal agreement with acquired lead CRi;
    and
    calculating, for integer i equal from 1 to 6, a time-aligned precordial lead Vi from time-aligned lead I, one of time-aligned lead II and time-aligned lead III, and one of time-aligned lead CRi and time-aligned lead CLi, for forming time-aligned precordial leads V1-V6;
  wherein time-aligned leads I-III, time-aligned augmented leads limb leads aVR, aVL, and aVF, and time-aligned precordial leads V1-V6 together form a standard 12-lead ECG.

In an embodiment, the system may be incorporated in a portable or wearable single-lead electronic device comprising said two electrodes and comprising said at least one processing unit configured to perform said acts. In some embodiments, all acts relating to sequentially acquiring the fifteen leads, and producing a standard 12-lead ECG therefrom, may be performed using such an electronic device only, without any need for further external devices. The electronic device may be a smartwatch, a smartphone, a dedicated ECG device, or the like. The two electrodes may be integrated in the electronic device, for instance formed at the exterior of a smartwatch, or be formed one or both as electrodes separate from the electronic device and connected by wire or wirelessly to the electronic device. In some embodiments, the electronic device may communicate with at least one external device, such as a smartphone, tablet, or computer, for certain functions such as for providing a user interface where the user may give and receive instructions, and for displaying the produced standard 12-lead ECG.

In an alternative embodiment, the system may be incorporated partly in a such a portable or wearable electronic device comprising two electrodes, and partly in at least one external device, said electronic device and said at least one external device being configured to communicate with each other. In such embodiment, the at least external device may comprise a smartphone, a tablet, a computer, or the like, and/or at least one external device comprising at least one server, such as a cloud server.

The at least one processing unit may be a central processing unit (CPU), which may execute the instructions of one or more computer programs in order to perform the acts of the inventive method, and optionally also to control the lead acquisition, including receiving user instructions and providing user instructions. The at least one processing unit may alternatively be implemented as firmware, or as a specifically designed processing unit. In the broadest aspect of the inventive concept, the at least one processing unit may be provided anywhere, such as in the "cloud".

The system according to the inventive concept may be configured to perform the acts of the method as defined in any of the method claims.

Advantages and embodiments discussed above in connection with the inventive method applies also to the system according to the inventive concept.

According to a third aspect of the inventive concept, there is provided a non-transitory computer-readable recording medium having recorded thereon a program which is executable on a processing unit having processing capabilities, wherein the program comprises program code portions which when executed on the electronic device are configured to perform the method according to any of the method claims.

The program may implement the method in at least one processing unit, which may be a dedicated processing unit for performing the method or may be a general-purpose processing unit which may be able to perform the method based on the computer program product.

The program product may be provided on a computer-readable medium provided with the computer-readable instructions, such as any computer-readable medium on which the computer-readable instructions may be stored. However, the program may also or alternatively be downloaded from a server, such that the program may be provided as a signal carrying the computer-readable instructions being downloaded.

Preferred embodiments of the inventive concept are set out in the dependent claims.

BRIEF DESCRIPTION OF THE DRAWINGS

The inventive concept, some non-limiting embodiments, and further advantages of the inventive concept will now be described with reference to the drawings in which:

FIG. 1 illustrates limb leads I-III.

FIG. 2 illustrates augmented limb leads VR, aVL, aVF.

FIGS. 9a-9c illustrate fifteen serial raw-data acquisitions, and corresponding average beat waveforms.

FIG. 16 is a schematic illustration of an embodiment of a system according to the inventive concept.

DETAILED DESCRIPTION

Figure 3:
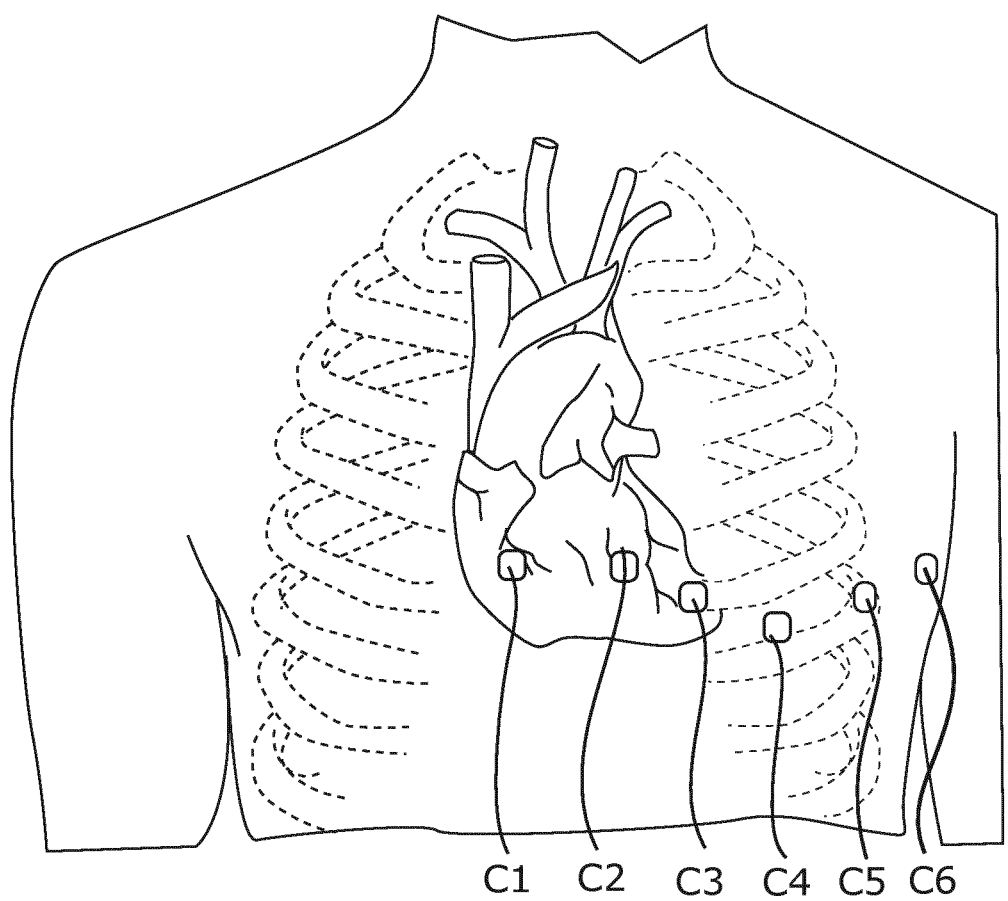
FIG. 3 illustrates standard chest electrodes C1-C6.

FIG. 1 illustrates the three standard limb electrode positions RA, LA, and LL, and also illustrates how the three standard limb leads I-III are measured between these electrodes. According to the AHA Standard, limb leads I-III are measured as follows:

$$I = \text{potential difference}_{LA-RA} \quad (1)$$

$$II = \text{potential difference}_{LL-RA} \quad (2)$$

$$III = \text{potential difference}_{LL-LA} \quad (3)$$

FIG. 2 illustrates the three standard augmented leads aVF, aVL, and AVR. While the three limb leads I-III are measured between physical electrodes, each one of the augmented limb leads aVR, aVL, and aVF are measured between an associated one of the three electrodes RA, LA, and LL, and an associated virtual electrode (termed the "Goldberger central terminal") representing the average of the two opposing electrodes. The augmented limb leads aVR, aVL, and aVF are calculated according to the AHA Standard as follows, using formulas (1)-(3) above to simplify:

$$aVF = LL - (LA + RA)/2 = (II + III)/2 \quad (4)$$

$$aVL = LA - (RA + LL)/2 = (I - III)/2 \quad (5)$$

$$aVR = RA - (LA + LL)/2 = -(I + II)/2 \quad (6)$$

FIG. 3 illustrates the six standard chest electrode positions C1-C6 used for measuring the six standard precordial leads V1-V6 in a standard 12-lead ECG. As described for the augmented limb leads above, each one of the six standard precordial leads V1-V6 is measured between an associated one of the physical electrodes C1-C6, and one virtual electrode. For the precordial leads V1-V6 a common virtual electrode is used, termed the Wilson Central Terminal, WCT, obtained by calculating the average of the three measured potentials at RA, LA, and LL:

$$WCT = (RA + LA + LL)/3 \quad (7)$$

Each standard precordial lead Vi (i=1 to 6) is calculated as:

$$Vi = \text{potential difference}_{Ci-WCT} \quad (8)$$

Accordingly, nine of the twelve standard leads forming a standard 12-lead ECG are calculated from virtual electrodes, which in their turn are calculated from two or more measured potentials. This fact represents a major challenge when using single-lead devices, since any calculation must be performed on time-synchronized leads. When only asynchronous, sequentially acquired data is at hand, a time-alignment becomes critical for obtaining a clinically reliable result since calculations require synchronous data. In conventional synchronous ECG machines this problem does not arise, since all calculations may be performed continuously during the recording time period on synchronous measured signals. As will be demonstrated below, it is extremely challenging to obtain sufficiently time-synchronized signals from non-synchronized ECG signals. Even the slightest incorrect time-shift, i.e. time-misalignment, may produce notable effects leading to incorrect, potentially misleading and non-useful ECGs. In prior-art attempts to produce multi-lead ECGs from asynchronous sequential data, the proposed methods have been to avoid the challenge especially with respect to the standard precordial leads V1-V6 and the WCT, and instead to use directly measured (non-calculated) and fewer, non-standard leads in the ECG. Deviations resulting from such solutions were discussed above in the above-mentioned VCG analysis.

One part of the inventive concept is based on the fact that each one of the precordial leads V1-V6 may be expressed in terms of measurement of the potential difference between a corresponding chest electrode Ci and an arm electrode:

For example, standard precordial lead V1 may be calculated as:

$$V1 = C1 - WCT = C1 - (LA + LL + RA)/3 = (3*C1 - LA - LL - RA)/3 = (3*(C1 - RA) - (LA - RA) - (LL - RA))/3 = (C1 - RA) - ((LA - RA) + (LL - RA))/3 = CR1 - (I + II)/3$$

where $$CR1 = C1 - RA$$

Thus, each precordial lead Vi, for integer i equal from 1 to 6, of the standard precordial leads V1-V6 may be calculated from measured leads CRi, I and II as follows:

$$Vi = CRi - (I+II)/3 \quad (9)$$

where $$CRi = Ci - RA \quad (10)$$

In the present disclosure, the leads CR1-CR6 measured between RA and C1-C6 are termed "arm-referenced chest leads". The leads CL1-CL6 measured between LA and C1-C6 are also termed "arm-referenced chest leads".

The present inventive concept is based partly on the insight that it is possible to "synthetize" the standard precordial leads V1-V6 of a standard 12-lead ECG from sequentially acquired, asynchronous leads using (9) and (10) above, provided that the three acquired leads CRi, I and II can be exactly time-aligned.

However, attempting to time-align the acquired ECG signals using time-alignment of averaged beats based on the peaks of the QRS complex will fail. The peak of the QRS complex cannot be used as a time reference for time-alignment because the QRS peak occurs at different time-points in different leads. Thus, using the peak of the QRS complex will result in an incorrect time-alignment and consequently an incorrect calculation of the precordial leads V1-V6.

The present inventive concept is based partly also on the insight that it is possible to "synthetize" the standard precordial leads V1-V6 of a standard 12-lead ECG from sequentially acquired, asynchronous leads if redundancy of information is used from non-standard leads, namely redundancy of information from both sequentially acquired arm-referenced chest leads CR1-CR6, and sequentially acquired arm-referenced chest leads CL1-CL6.

The inventive concept involves acts of time-alignment and acts of calculations. These acts may be performed in various orders. A first non-limiting embodiment will now be described with reference to FIGS. 4 to 8, and FIGS. 9A-9C, where the sequential acquisition is performed by using a single-lead electronic device, here in the form of a smartwatch 10, comprising two electrodes, a display, a processing unit, and a program (app) which when executed on the processing unit is configured to perform the acts described below. A first electrode is located on the rear side of the smartwatch, and a second electrode is formed by the crown 12, and/or the frame, and/or some other distinctly touchable portion of the smartwatch 10. All variants of the second electrode will collectively be referred to herein as the "crown".

Figure 9B:
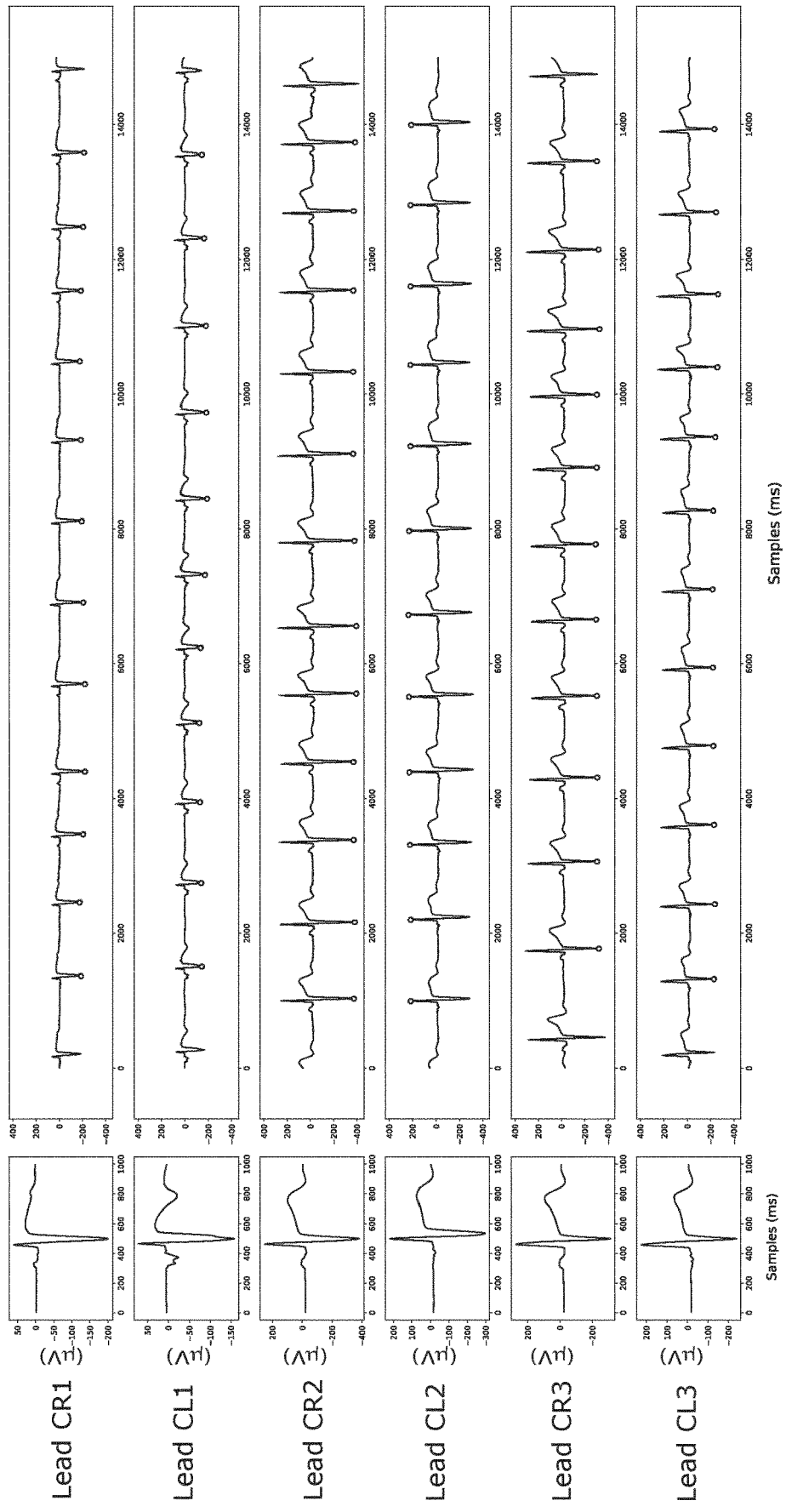
Figure 9C:
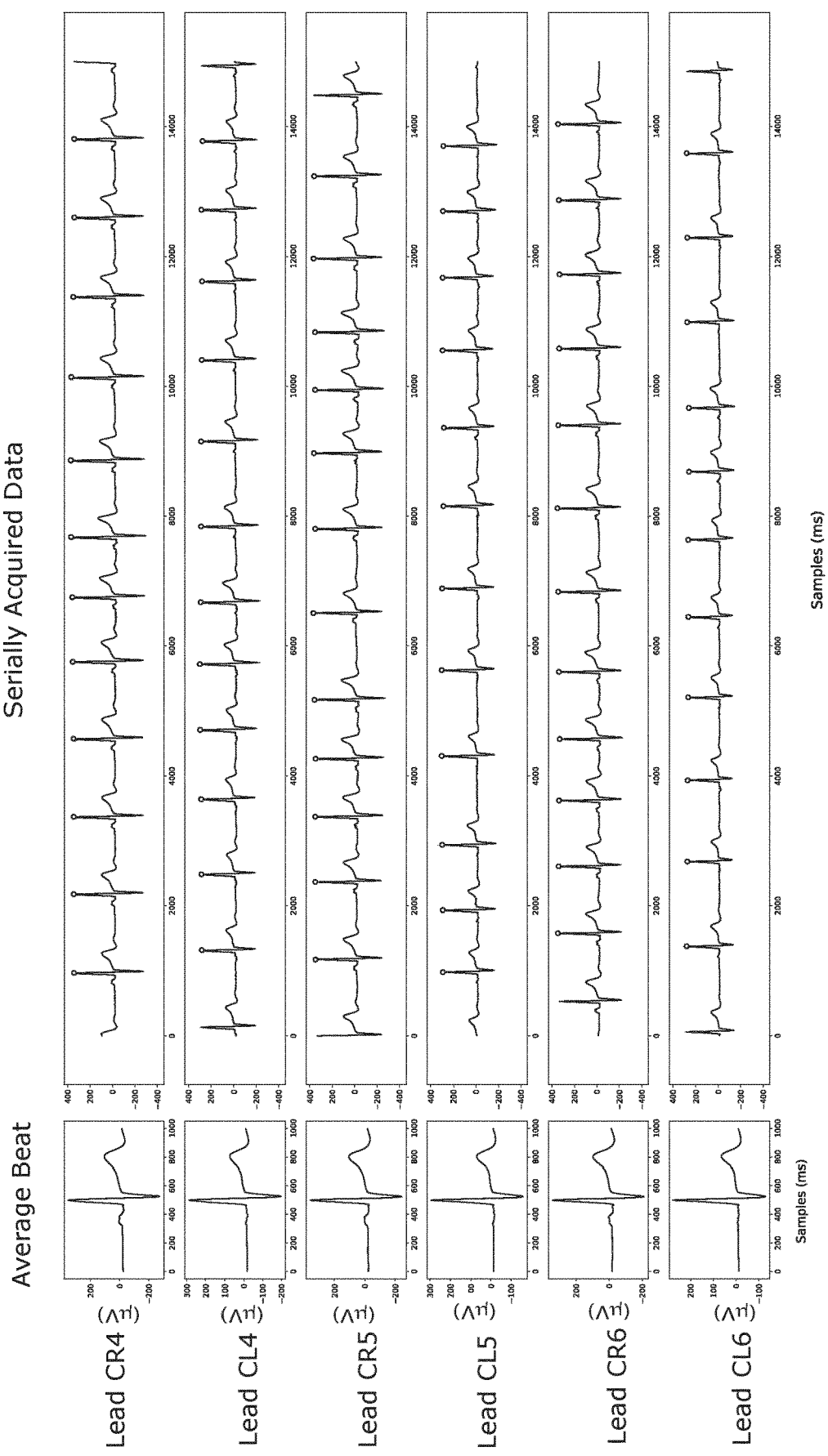

Fifteen specific leads are sequentially acquired: three limb leads I-III, six arm-referenced chest leads CR1-CR6, and six arm-referenced chest leads CL1-CL6. FIG. 9a-9c shows to the right the fifteen waveforms recorded from a subject during a time period of 15 seconds. This is the raw data from fifteen sequential acquisitions from one representative subject, required to perform time-alignments and calculations for forming a standard 12-lead ECG according to the inventive concept. The small circles show the detection of the maximal deflection of the QRS complex, which is used to align the recordings for forming average beat waveforms shown to the left in FIGS. 9a-9c.

Figure 4:
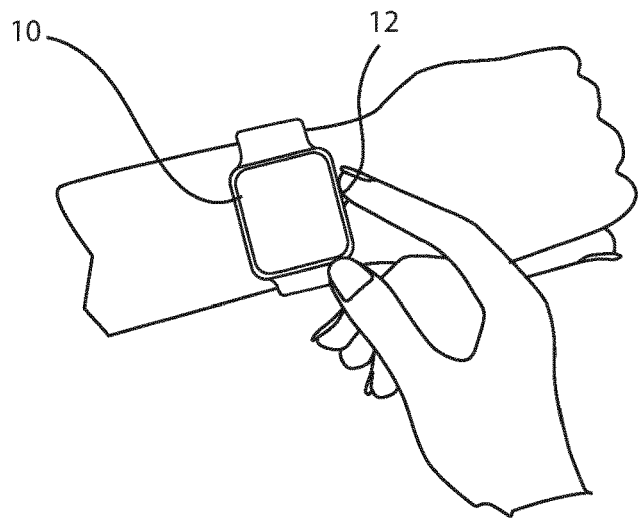
FIG. 4 illustrates a smartwatch positioned for acquiring a limb lead.
Figure 7:
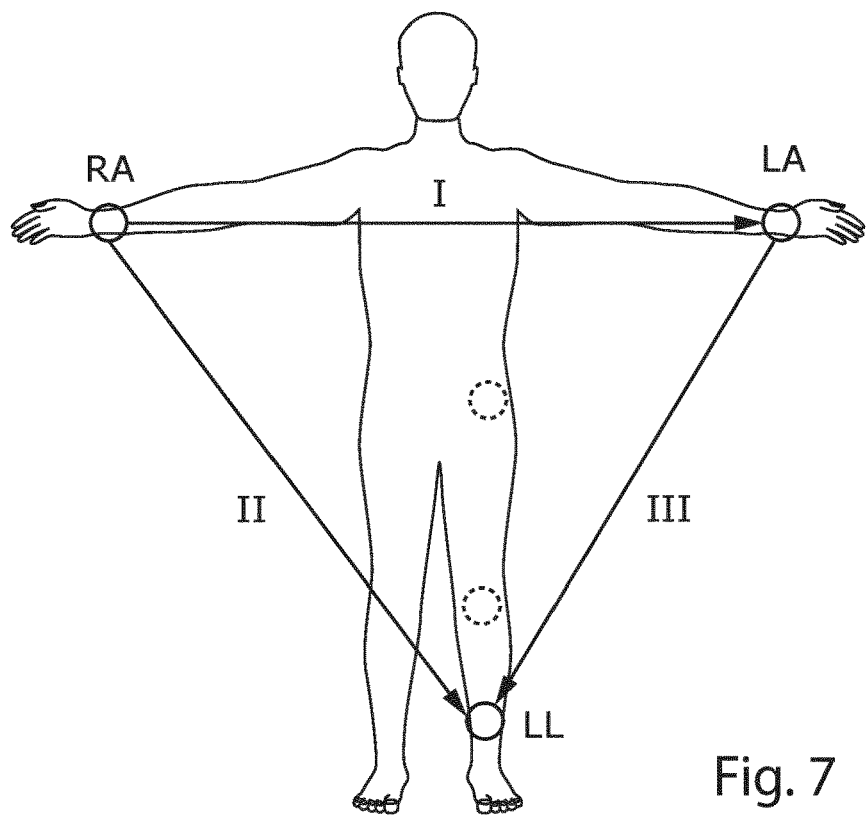
FIG. 7 illustrates time-alignment of limb leads I-III.

In this non-limiting embodiment, limb leads I-IIII are first recorded as illustrated in FIG. 4 and FIG. 7. The smartwatch 10 is initially attached to, or held on, the left wrist of the subject with a first electrode on the backside of the smartwatch being in contact with electrode position LA. The right-hand index finger contacts the crown 12 thereby closing the circuit. The second electrode position corresponds to electrode position RA. The limb lead I (LA-RA) is recorded for a time period representing at least one heartbeat, preferably a plurality of heart beats for a subsequent averaging. In the illustrated case, all leads were recorded for a period of 15 seconds. Thereafter, limb lead II and limb lead III are recorded by holding the smartwatch 10 with its rear-side electrode in contact with electrode position LA and LL, respectively. For measuring lead II (LL-RA), the right hand is held in contact with the crown 12, and for measuring lead III (LL-LA), the left hand is held in contact with the crown 12. Electrode position LL may be at any position on the left leg (ankle, knee) or at the lower left side of the abdomen, as shown with dashed electrode positions in FIG. 7. In this way, three sequentially acquired limb leads I-III are obtained and saved in the memory of the smartwatch 10. The sequentially acquired data is shown to the right in FIG. 9a.

Figure 5:
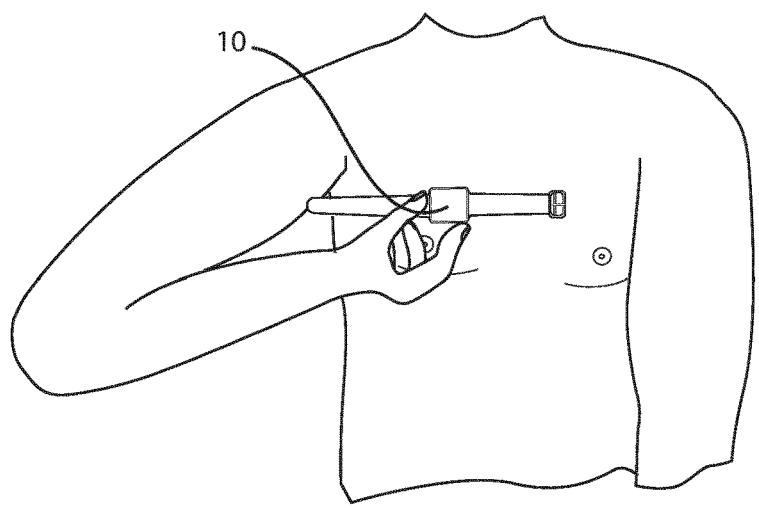
FIGS. 5 and 6 illustrate a smartwatch positioned for acquiring two arm-referenced chest leads.
Figure 6:
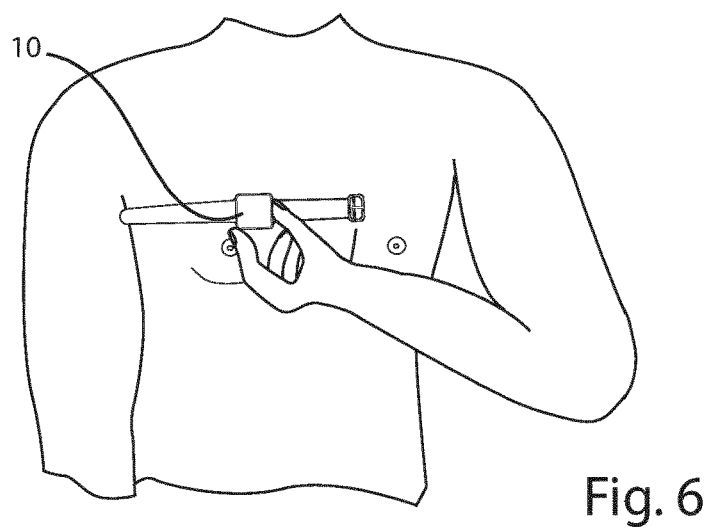
Figure 8:
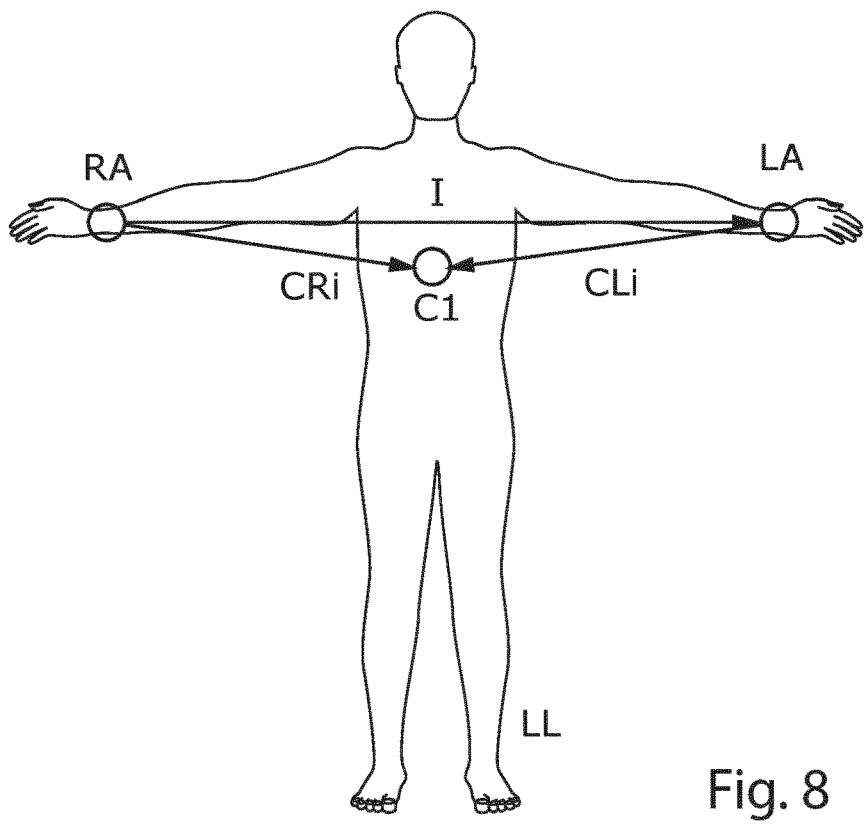
FIG. 8 illustrates time-alignment of arm-referenced chest leads CR1-CR6, and CL1-CL6.

Subsequently, twelve arm-referenced chest leads CR1-CR6 and CL1-CL6 are sequentially measured as illustrated in FIGS. 5, 6 and 8. With reference to FIG. 5, the user initially holds the smartwatch 10 with the rear-side electrode in contact with the chest at electrode position C1, and with the right hand in contact with the crown 12 (second electrode) for closing the circuit. In this position, lead CR1=C1-RA (FIG. 8) is recorded. Thereafter, while maintaining the smartwatch 10 in the same position as shown in FIG. 6, the user instead contacts the crown 12 with the left hand for recording lead CL1 (FIG. 8) between electrodes LA and C1. This procedure is repeated for sequential recording of all lead pairs CRi and CLi. In this way, twelve arm-referenced chest leads CR1-CR6 and CL1-CL6 are sequentially recorded and saved in the memory of the smartwatch 10. The recorded waveforms are shown to the right in FIGS. 9b and 9c.

In order to optimize the accuracy of the time-alignment and calculations to be performed, it is beneficial to create an average beat waveform for each one of the fifteen acquired leads shown to the right in FIGS. 9a-9c. The program is preferably configured to perform such averaging when executed. The averaging may be performed by aligning all beats to the peak of the QRS complex (marked with small circles in the recorded data), to form a corresponding averaged beat waveform for each acquired lead. The resulting fifteen averaged beat waveforms are illustrated to the left in FIGS. 9a-9c, and are used for the subsequent time-alignments and calculations. Each one of the resulting twelve standard leads forming the aimed-at standard 12-lead ECG will also be in the form of a beat waveform. It should be noted, as mentioned above, that such time-alignment using the peak of the QRS complex cannot be used to time-align different leads with one another, only for aligning beat waveforms of a common lead for averaging purposes.

There is a redundancy of information of the acquired limb leads I-III which may be used to form time-aligned limb leads I-III, based on the formula:

$$\text{Lead } III = \text{Lead } II - \text{Lead } I \quad (11)$$

Formula (11) may be seen as the vector sum I+III=II in FIG. 7. Lead III can be calculated as lead II−lead I, but the time-shift between sequentially acquired lead I and lead II is unknown. In some embodiments, this subtraction may be performed while iteratively shifting the time-alignment between I and II until an optimal agreement between calculated lead III and acquired lead III is achieved. The program of the watch may be configured to perform such time-alignment. The difference between calculated lead III and acquired lead III will be at its minimum when the optimal time-alignment has been achieved between lead I and lead II. As an example, acquired lead I may be used as reference, while acquired lead II is time-shifted. In this manner, time-aligned leads I and II may be formed. Time-aligned lead III may be calculated using formula (11) above. In the present embodiment where averaged beat waveforms have been created, the time-alignment and the calculations are performed on the averaged beat waveforms, and the resulting time-aligned leads I-III will be in the form of beat waveforms as illustrated to the left in FIG. 9a.

Using formulas (4) to (6) above, time-aligned augmented leads aVR, aVL, and aVF are calculated by the processing unit of the watch, from the accurately time-aligned leads I-III. The calculated augmented leads aVR, aVL, and aVF will also be in the form of beat waveforms.

Contrary to the situation with the standard limb leads I-III which are measured between physical electrodes, the standard precordial leads V1-V6 are conventionally calculated from the virtual WCT according to formulas (7) and (8) above when using a conventional ECG machine. However, due to the specific redundancy of information acquired by sequentially recording both the six arm-referenced chest leads CR1-CR6 and the six arm-referenced chest leads CL1-CL6, it is possible to perform an exact time-alignment which eventually makes it possible to correctly calculate the six standard precordial leads V1-V6 from the time-aligned leads, with a high level of accuracy.

In one embodiment and with reference to FIG. 8, a time alignment is performed between time-aligned lead I and acquired arm-referenced lead CR1, using acquired lead CL1 as an alignment reference, and using the formula CL1=CR1−I. CL1 may be time shifted in relation to lead I which is already time-aligned with II and III. By performing similar time-alignment using all pairs CRi and CLi, six time-aligned leads CR1-CR6 may be formed using the formula (i=1-6):

$$CLi=CRi-1 \tag{12}$$

The time alignment of each one CRi of the six acquired arm-referenced chest leads CR1-CR6 may be performed by iteratively shifting the time-alignment of acquired $CRi_a$, where the subscript a denotes an acquired lead, in relation to the already time-aligned acquired lead $I_a$ until the difference between a calculated lead $CLi_c$, where the subscript c denotes a calculated lead, calculated from the acquired values of $CRi_a$ and $I_a$ as, $$CLi_c=CRi_a-I_a \tag{13}$$

and the acquired reference value of $CLi_a$ is at a minimum.

Following the above time-alignments and calculations performed by the processing unit, three time-aligned leads I and II, and six time-aligned leads CR1-CR6 are now available. Since all these leads are time-aligned with each other, they may be used for calculations. Using formula (9) above (Vi=CRi−(I+II)/3), the six time-aligned standard precordial leads V1-V6 may now be calculated by the processing unit from time-aligned I, time-aligned II and time-aligned CR1-CR6.

It may be noted that the process creating the standard precordial leads V1-V6 from sequential data differs from the process of time aligning standard limb leads I-III. In creating V1-V6, the time-alignment is performed using twelve sequentially acquired leads which are not part of the set of twelve standard leads. For obtaining each precordial lead Vi of V1-V6, the inventive concept uses two measurements on the associated chest electrode Ci and acquisitions of leads not forming part of the standard ECG.

Figure 12:
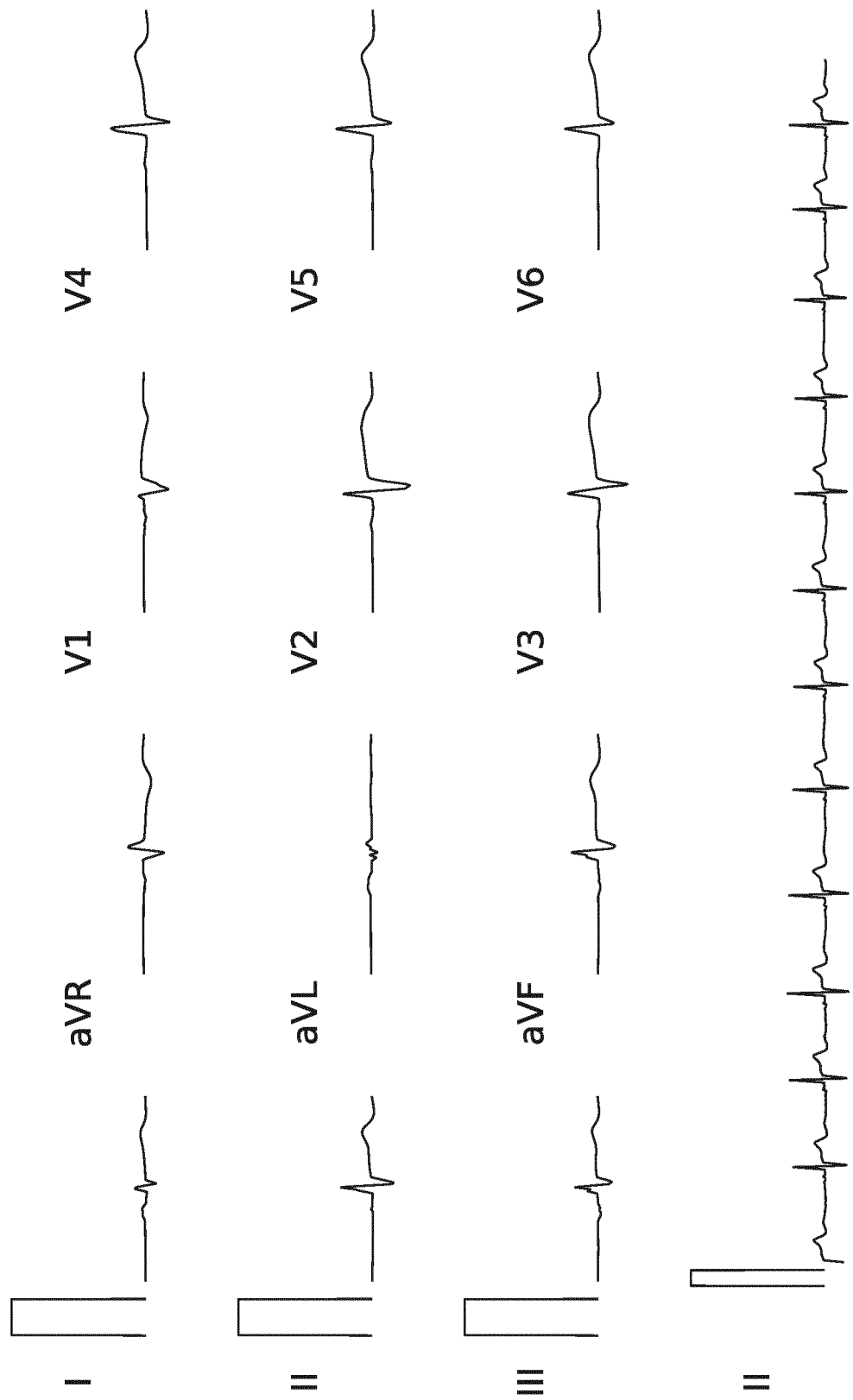
FIG. 12 illustrates a standard 12-lead ECG produced by an embodiment of the invention.

FIG. 12 illustrates an example of a standard 12-lead ECG obtained by the inventive method, formed by the three time-aligned standard limb leads I-III, the three time-aligned standard augmented leads aVR, aVL, and aVF, and the six time-aligned standard precordial leads V1-V6, created from the initially asynchronous fifteen acquired leads in FIGS. 9a-9c. Each one of the twelve standard leads in FIG. 12 is in the form of an averaged beat waveform. At the bottom of the ECG in FIG. 12, there is also, in one embodiment, included acquired limb lead II as measured over a period of time covering multiple heartbeats. Other embodiments may also, or alternatively, display any combination of the fifteen leads acquired over a period of time covering multiple heartbeats.

Within the scope of the inventive concept, the precordial leads V1-V6 may be calculated by using variants of formula (9). First, because of the relationship between lead II and lead III according to formula (11) any of lead II and lead III may be used for the Vi calculation. Furthermore, because of the relationship between lead CLi and lead CRi according to formula (12) above, any of CLi and CRi may be used for calculating Vi.

As an example, using step (b) in claim 1, one or more of the six standard precordial leads V1-V6 may be calculated by instead time-aligning leads CL1-CL6 with time-aligned lead I, using CR1-CR6 as reference and the formula:

$$CRi=CLi+I \tag{12'}$$

and time-shifting each acquired lead $CLi_a$ in relation to time-aligned lead I until a difference between a calculated lead $CRi_c$ (calculated as the sum of acquired $CLi_a$+time-aligned acquired $I_a$) and acquired $CRi_a$ is at a minimum, representing an optimal alignment. Accordingly, any number of the six precordial leads V1-V6 may also be calculated from time aligned CLi and time-aligned III and I as:

$$Vi=CLi-(III-I)/3 \tag{14}$$

Furthermore, each one of the precordial leads V1-V6 may be calculated either from a time-aligned acquired version of CRi or CLi as described above, or from a time-aligned calculated version of CRi or CLi. For instance, as an alternative of using time-aligned acquired CRi for calculating Vi as described in the above example, it is possible to instead calculate Vi from a time-aligned calculated version of CLi using formula (14), where time-aligned CLi is calculated from time-aligned CRi and time-aligned I obtained in step (a). In the same way, each Vi may also be calculated from a time-aligned calculated version of CRi, where time-aligned CRi is calculated from time-aligned acquired CLi and time-aligned I obtained in step (b).

The order of time-alignment and calculation is not essential, and the inventive concept is considered to cover all possible orders as long as the calculations are performed on the required time-aligned values.

As an alternative, it is possible to start with the time-alignment of lead I and the arm-referenced chest electrodes, and thereafter create time-aligned leads I-III.

The calculation of the six precordial leads V1-V6 may be performed when all time-alignment has been performed. As an alternative, each precordial lead Vi may be calculated as soon as the corresponding time-aligned leads needed for the calculation of Vi have been formed.

In some embodiments, all fifteen acquisitions may be performed before any averaging, time-alignment, and calculation is performed. In other embodiments, one or more of the acts of time-averaging, time-alignment, and calculation may be performed once the data required for the respective act is available.

Figure 10:
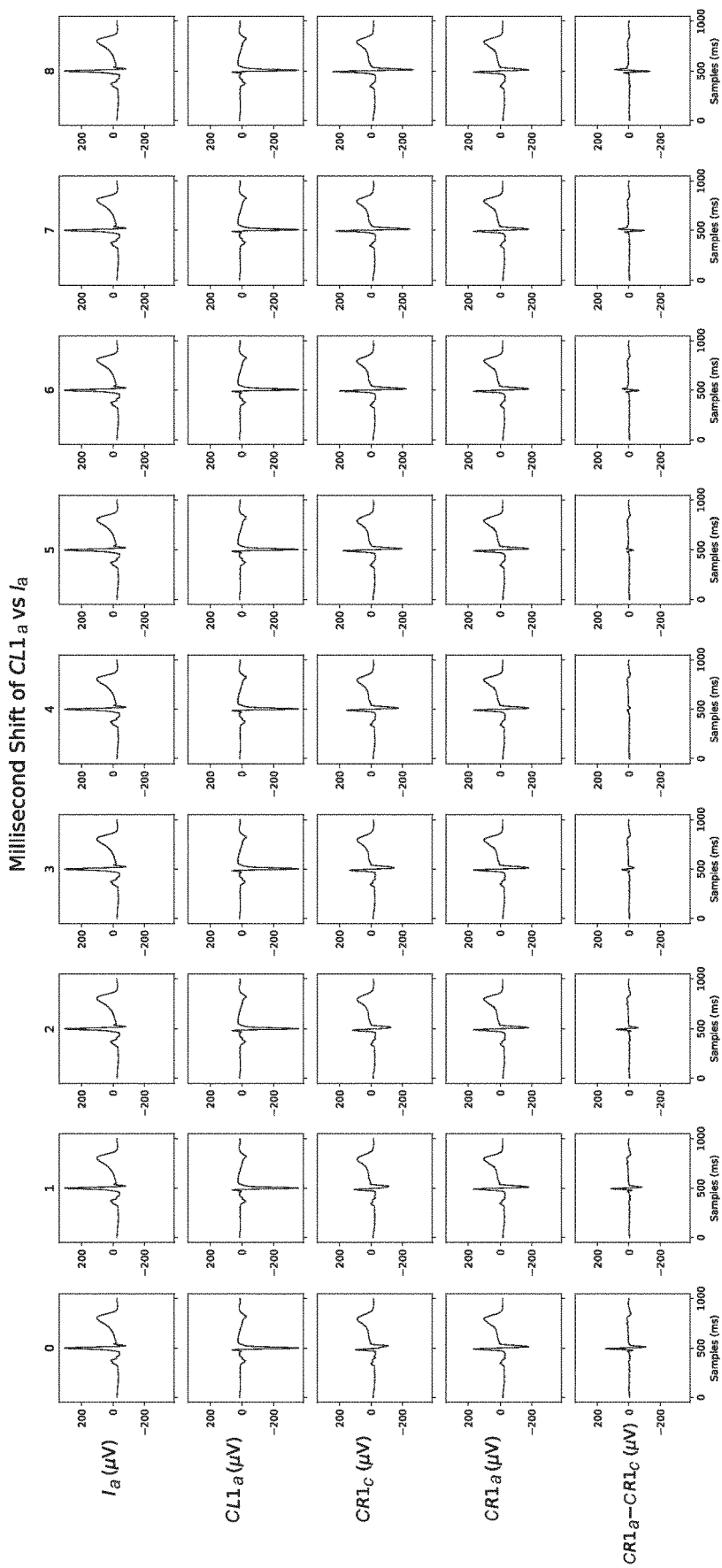
FIG. 10 illustrate the effect of time-alignment.

Reference is now made to FIG. 10, which illustrates how critical it is to obtain a very exact time-alignment in order to subsequently achieve correctly calculated values from the time-aligned values. The beat waveforms in FIG. 10 were obtained from a study performed by the inventors on a subject using the inventive concept. Each beat waveform is shown over a period of 1000 ms. FIG. 10 illustrates the effect of slightly changing a time shift, within a range of 0 to 8 ms, between acquired lead $CL1_a$ and acquired lead $I_a$. In FIG. 10, subscript "a" means "acquired", and subscript "c" means "calculated".

The $1^{st}$ row in FIG. 10 shows acquired lead $I_a$. The $2^{nd}$ row shows acquired lead $CL1_a$. The $3^{rd}$ row shows calculated lead $CR1_c = I_a + CL1_a$ according to formula (12). The $4^{th}$ row shows acquired lead $CR1_a$. When time-aligning acquired lead $CL1_a$ with acquired lead $I_a$ in the two top rows, calculated lead $CR1_c$ should match acquired lead $CR1_a$ as closely as possible, i.e. the difference $CR1_a - CR1_c$ therebetween should be as small as possible. The $5^{th}$ row in FIG. 10 shows the difference $CR1_a - CR1_c$ for different time-shifts, in steps of 1 ms. In other embodiments, the time shift may be in shorter or longer intervals than 1 ms in order to optimize the time-alignment. In this example, the optimal time-alignment is achieved for a time-shift of 4 ms, resulting in a difference being effectively zero in the $5^{th}$ row. An incorrect time-shift by just one or a few milliseconds (keeping in mind that the whole waveform is about 1000 milliseconds long) produces a noticeable incorrect match, as shown for instance at the right-most and the left-most waveforms in the $5^{th}$ row. Accordingly, even the slightest incorrect time-shift in the time-alignment may produce an incorrectly calculated value of Vi. The almost zero-value obtained for a time-shift of 4 ms will thus produce the most correctly calculated lead V1.

Figure 11A:
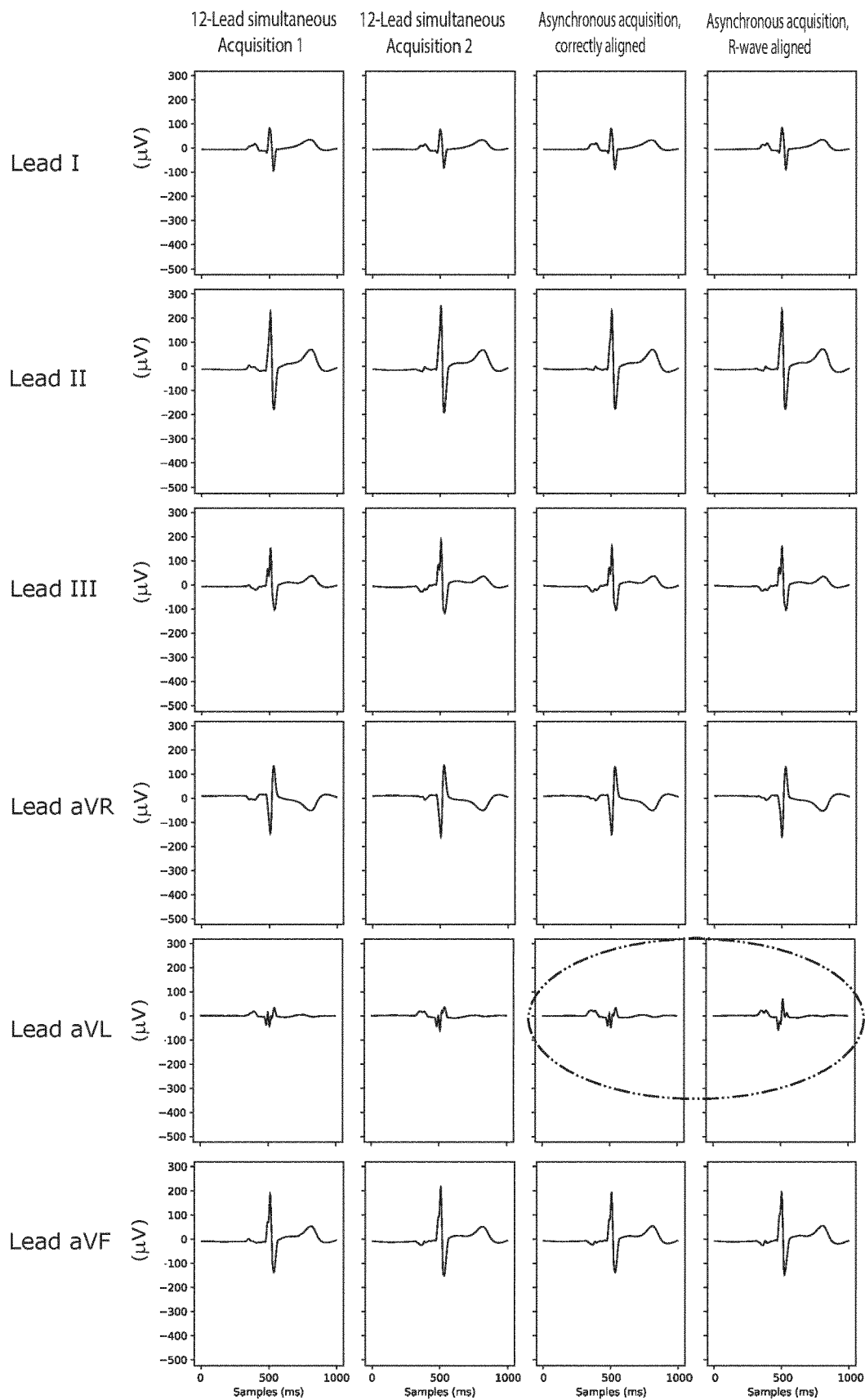
FIG. 11a-11c illustrate waveforms demonstrating the accuracy of the inventive concept.
Figure 11B:
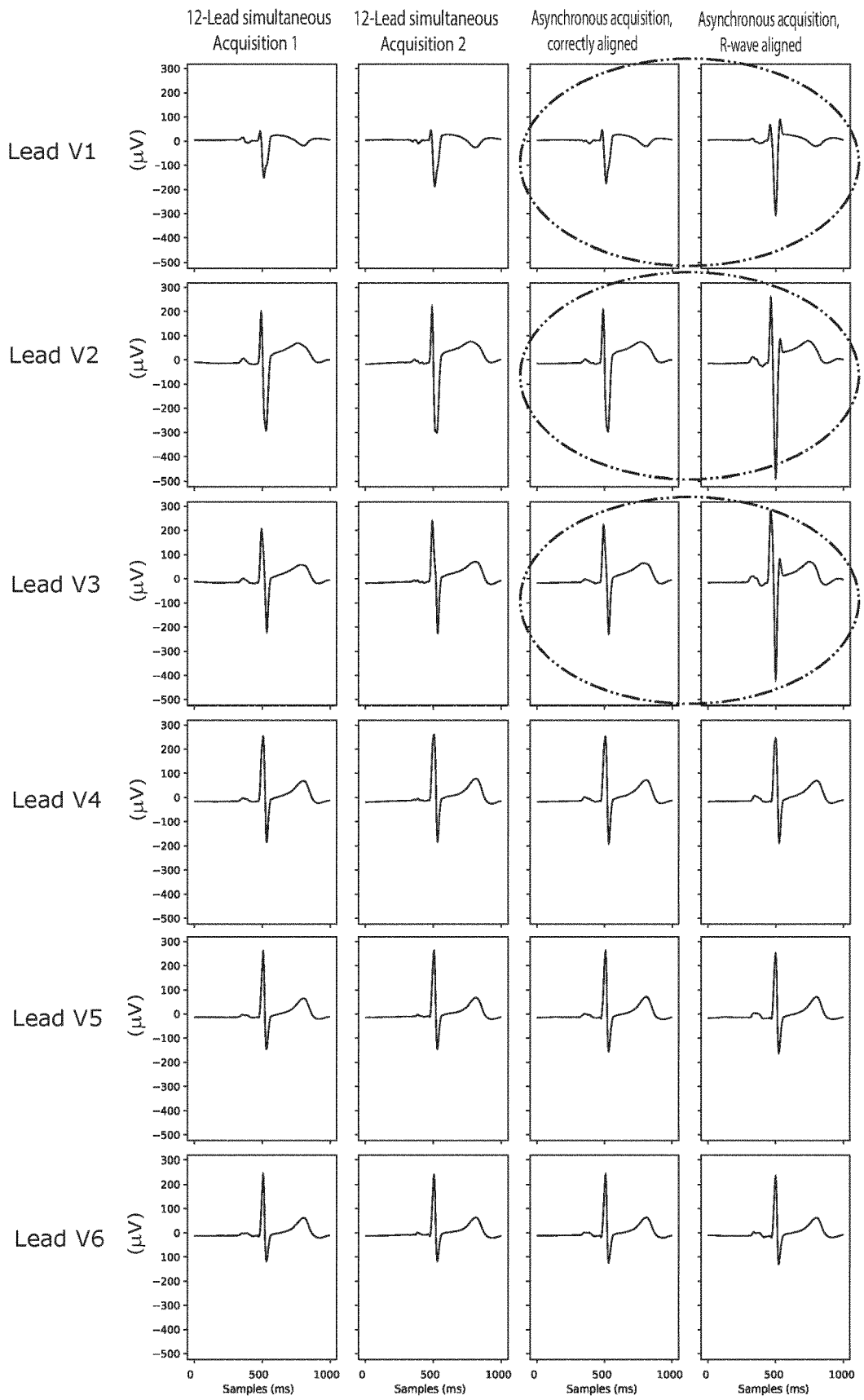

Reference is now made to FIGS. 11a and 11b which show limb leads I, II, III, aVR, aVL, and aVF from the same subject as in FIGS. 9a-9c. This is the result from a study performed by the inventors comparing, on the one hand, the result from serial acquisitions of the fifteen leads and subsequent alignment and calculation according to the inventive concept, with, on the other hand, the result of a conventional simultaneous acquisition of all twelve leads.

The first two columns labeled "12-lead simultaneous, Acquisition 1" and "12-lead simultaneous, Acquisition 2" show two separate simultaneous acquisitions recorded by a synchronous conventional 12-lead ECG machine, representing "true" leads. The third column "Asynchronous acquisition, correctly aligned" shows the results obtained by the inventive concept by performing time-alignment and calculations according to the inventive concept, based on the sequential acquisitions from FIG. 9a-9c from the same subject. The fourth column "Asynchronous acquisition, R-wave aligned" shows the "unaligned" results obtained when time-alignment was not performed according to the inventive concept, but only using the maximum deflection of the QRS complex as reference for time-aligning the acquired leads. The most noticeable differences are highlighted by a circle, such as for V1, V2, and V3. FIGS. 11a and 11b also clearly show the excellent match between the "true" leads in the two first columns and the result obtained by the inventive concept.

Derived Vectorcardiography, VCG

TABLE I

|   | I     | II    | V1    | V2    | V3    | V4    | V5    | V6   |
|---|-------|-------|-------|-------|-------|-------|-------|------|
| X | 0.38  | −0.07 | −0.13 | 0.05  | −0.01 | 0.14  | 0.06  | 0.54 |
| Y | −0.07 | 0.93  | 0.06  | −0.02 | −0.05 | 0.06  | −0.17 | 0.13 |
| Z | 0.11  | −0.23 | −0.43 | −0.06 | −0.14 | −0.20 | −0.11 | 0.31 |

Table I above is a matrix according to Kors, showing the coefficients with which one multiplies and sums the values of leads I, II, and V1-V6 in order to calculate derived Frank leads X, Y, and Z for a VCG. Thus, the Frank leads X, Y, and Z may be derived (calculated) mathematically from the eight standard leads I, II, and V1-V6 created using the inventive concept, since these leads are all time-aligned. Accordingly, the inventive concept also makes it possible to perform VCG analysis on sequentially acquired ECG signals, and as a result also advanced diagnostic algorithms based on the VCG leads.

For example, Frank lead X may be calculated as follows using the matrix above:

$$X = 0.38I - 0.07II - 0.13V1 + 0.05V2 - 0.01V3 + 0.14V4 + 0.06V5 + 0.54V6$$

Figure 11C:
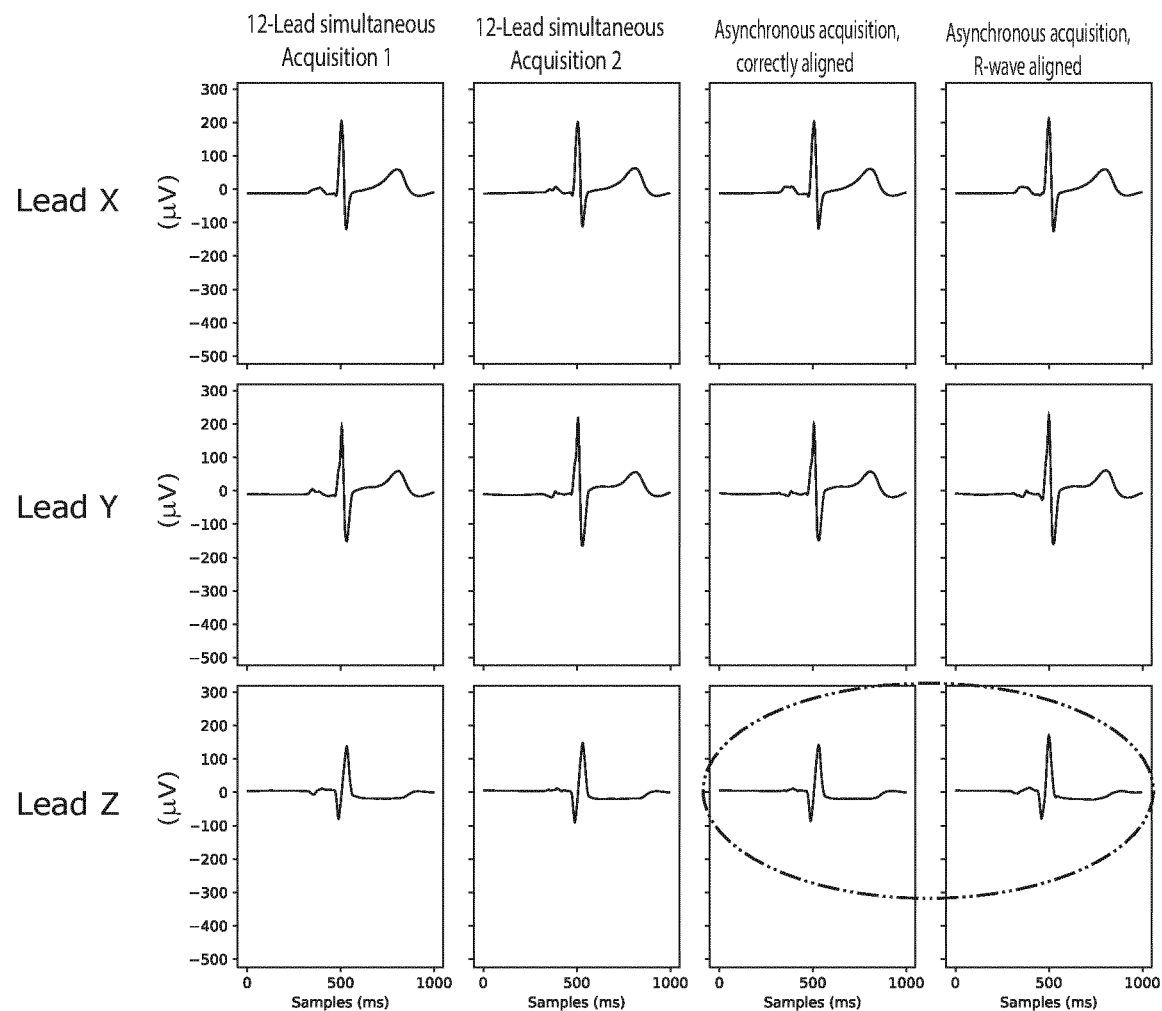
Figure 13:
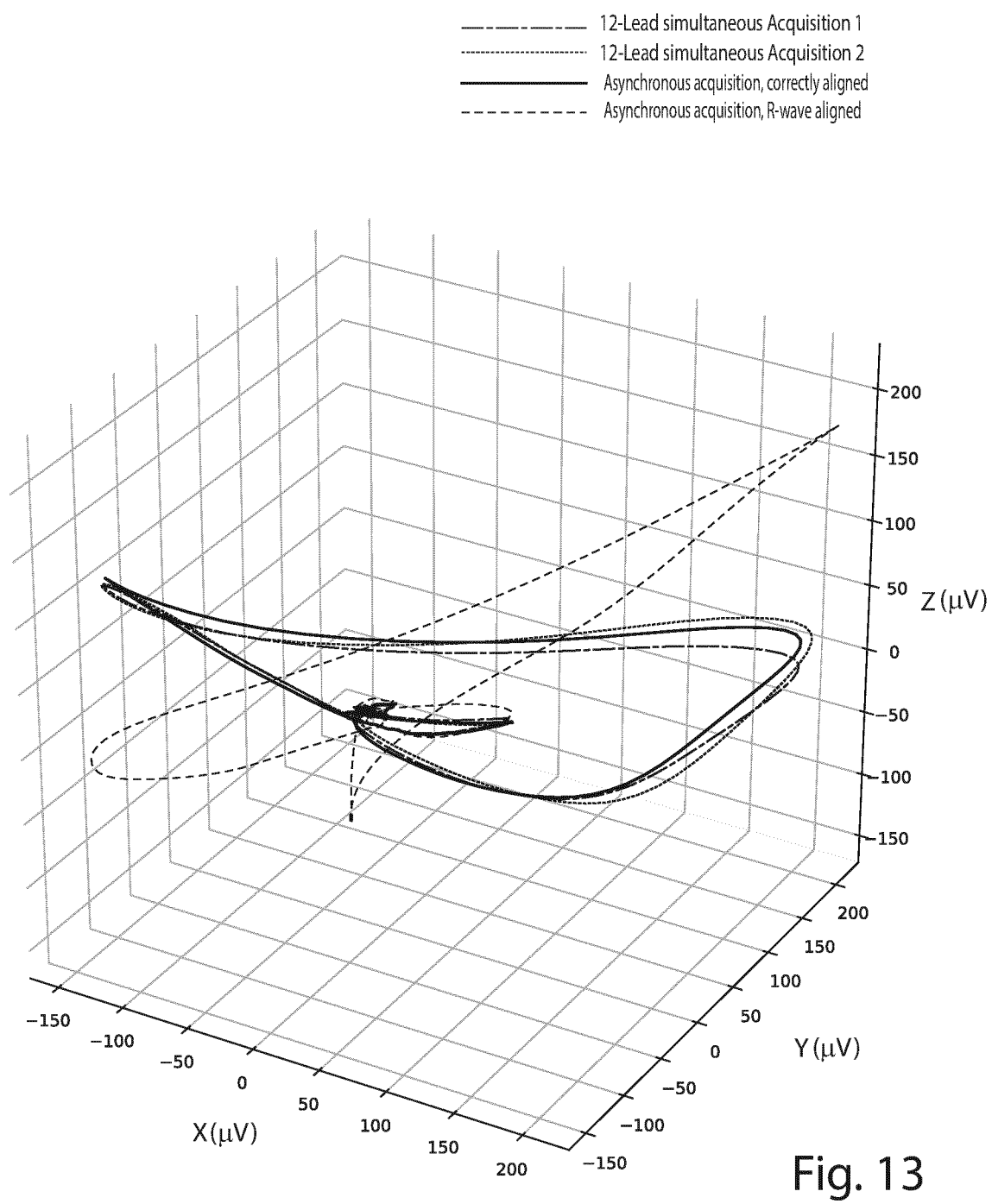
FIG. 13 is a three-dimensional VCG plot produced by an embodiment of the invention.

FIG. 11c and FIG. 13 show the results of generating leads X, Y, and Z from the leads I, II, and V1-V6 obtained by the inventive concept. A subtle deviation is especially noted in lead Z when QRS time-alignment is not used. However, the substantial advantage obtained by the invention is perhaps even better appreciated in a graphical VCG plot.

FIG. 13 shows a three-dimensional plot of the derived X, Y, and Z leads in FIG. 11c. The same labels are used as in FIG. 11c. The first two represent the results using separate simultaneous acquisitions of the 12-lead ECG. The curve drawn with a thicker solid line represent the results obtained from time-aligning and calculation based on sequential acquisitions according to the inventive concept. The fourth curve drawn with a dashed line shows the "unaligned" results when time-alignment was performed only with the maximum deflection of the QRS complex, and without using the inventive concept. The VCG analysis in FIG. 13 clearly demonstrates how the inventive concept (solid black line) shows excellent agreement with the true reference values, whereas the dashed curve shows substantial differences.

Optional Additional Averaging

As mentioned in the summary section, the redundancy of information present in the fifteen acquired leads may optionally be used for obtaining additional advantages, including noise-reduction and/or reduced acquisition time, by averaging acquired versions and a calculated versions of the leads, thereby utilizing all the available redundant information as much as possible. The averaging is performed by at least one processing unit. In the description and the calculations given below as examples using this technique, acquired leads are identified by subscript "a", calculated leads are identified by subscript "c", while resulting averaged leads are identified by underscore. A general formula may be written as follows, while it is understood that other types of averaging also may be considered:

Lead $\underline{X} = (\text{Lead } X_a + \text{Lead } X_c)/2$

For lead III, such an additional averaging may be performed as follows: If $I_a$ and $II_a$ are time-aligned using $III_a$ as a reference for forming time-aligned $I_a$ and time-aligned $II_a$, then a calculated time-aligned lead $III_c$ can subsequently be calculated as:

time-aligned $III_c$ = time-aligned $II_a$ − time-aligned $I_a$

Two versions of lead III are now available, both time-aligned: one acquired version $III_a$, and one calculated version $III_c$. Since the two versions are time-aligned with each other, they can be averaged as:

$$III=(III_a+III_c)/2$$

The obtained averaged lead III has been obtained by using the redundancy of information and can present a lower noise level.

Averaged lead I may be calculated in the same way by first time-aligning $II_a$ and $III_a$ using $I_a$ as a reference, thereafter calculating time-aligned $I_c$ from time-aligned $II_a$ and $III_a$, and finally by calculating averaged $I=(I_a+II_c)/2$.

Averaged lead II may be calculated in the same way.

Averaged augmented leads aVR, aVL, and aVF may be calculated by averaging the augmented leads generated from any two combinations of acquired leads I and II, II and III, or I and III. Alternatively, leads aVR, aVL, and aVF will be the result of calculating these leads when using the above averaged leads I, II, and III.

Each averaged precordial lead Vi may be calculated from averaged CRi, I and II as Vi=CRi−(I+II)/3. As an alternative, formula (14) and CLi may be used instead. In this example, averaged CRi may be calculated as the average of an acquired version and a calculated version of CRi:

$$CRi=(CRi_a+CRi_c)/2$$

The calculated version $CRi_c$ may be calculated using formula (10) as:

$$CRi=Ci-RA$$

Thereafter, each averaged Vi may be calculated using formula (9) as:

$$Vi=CRi-(I+II)/3$$

By using this averaging technique and all of the redundancy of information in the acquired signals, the acquisition time may be shortened while maintain noise at the same level. As an example, it may be possible to produce a standard 12-lead ECG from sequentially acquisitions each being about only 5 seconds long. Obviously, a shortened acquisition time is especially beneficial when the ECG acquisitions have to be sequentially recorded.

Example I

Figure 14:
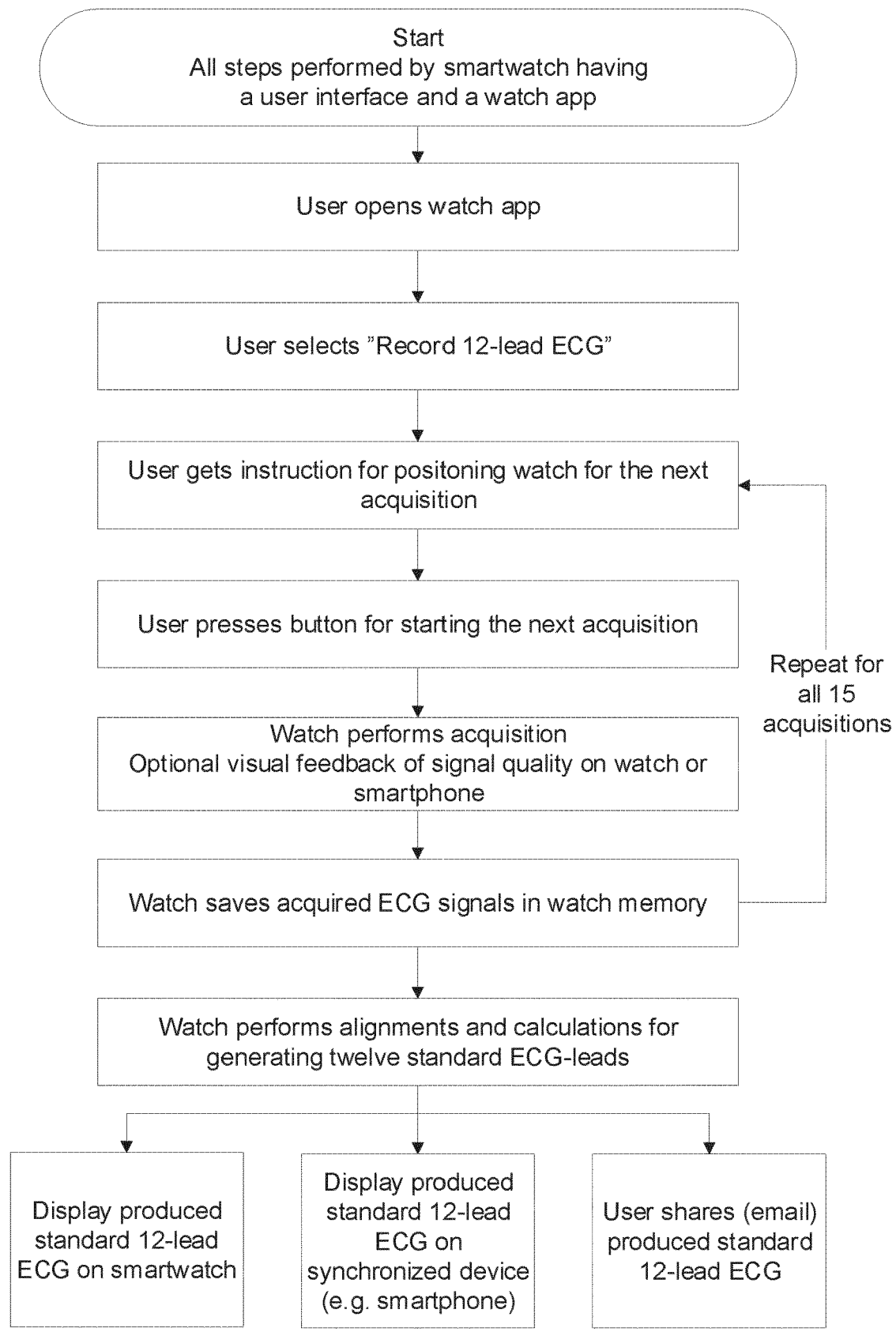
FIG. 14 is a flowchart illustrating acts of an embodiment of the invention.

FIG. 14 illustrates a flowchart including a sequence of acts for producing a standard 12-lead ECG according to an embodiment of the inventive concept. In this embodiment, all time-alignment and calculations for generating the standard twelve ECG leads from fifteen sequentially acquired ECG leads may be performed in a smartwatch, such as the smartwatch 10 in FIGS. 4 to 6. However, optionally the smartwatch may be connected to a smartphone, a tablet, a computer, or the like, for providing enhanced user experience and functionality. The smartwatch 10 has a user interface, at least one processing unit, and a non-transitory computer-readable recording medium having thereon a program, termed "watch app", configured to perform the steps illustrated in the flowchart.

In the first step, the user opens the watch app. At this point in time, the user may as a non-limiting example be wearing the smartwatch on one wrist as shown in FIG. 4. On the user interface (or on a connected smartphone or the like), the user initiates the procedure by selecting "Record 12-lead ECG". The watch provides visible and/or audible instructions for positioning the watch and hands for the next acquisition. If a smartphone or the like is in communication with the smartwatch, it may provide the instructions also, for instance graphical instructions for positioning the smartwatch. For instance, the first instruction may be to hold the watch as shown in FIG. 4 for acquisition of lead I. Thereafter, the user instructs the watch "next" to start the first acquisition. As non-limiting examples this may be performed by pressing a button on the display, pressing a physical button, giving audible instructions, or otherwise. The watch now performs the acquisition of the first lead over a predetermined time period. During the acquisition, the ECG signal quality may optionally be presented on the display of the watch. This may be beneficial to see for a second person (a doctor, a nurse, a paramedic, other healthcare professional, other assisting person, etc.) who may be helping the person to record an ECG, or who is doing it completely for the person. At the end of each acquisition, the acquired ECG signal is saved in a memory of the watch. The above sequence is repeated for all leads as illustrated in FIG. 14. At the conclusion of the final $15^{th}$ acquisition, the watch app performs the alignments and calculations described above, to generate the 12-lead ECG. As mentioned above, the acquired raw data may optionally be saved for various purposes.

The produced 12-lead ECG may be displayed on the smartwatch, displayed on a larger display of an external synchronized electronic device (e.g. a smartphone, a tablet, or a computer), and be shared via e.g. email.

Example II

Figure 15:
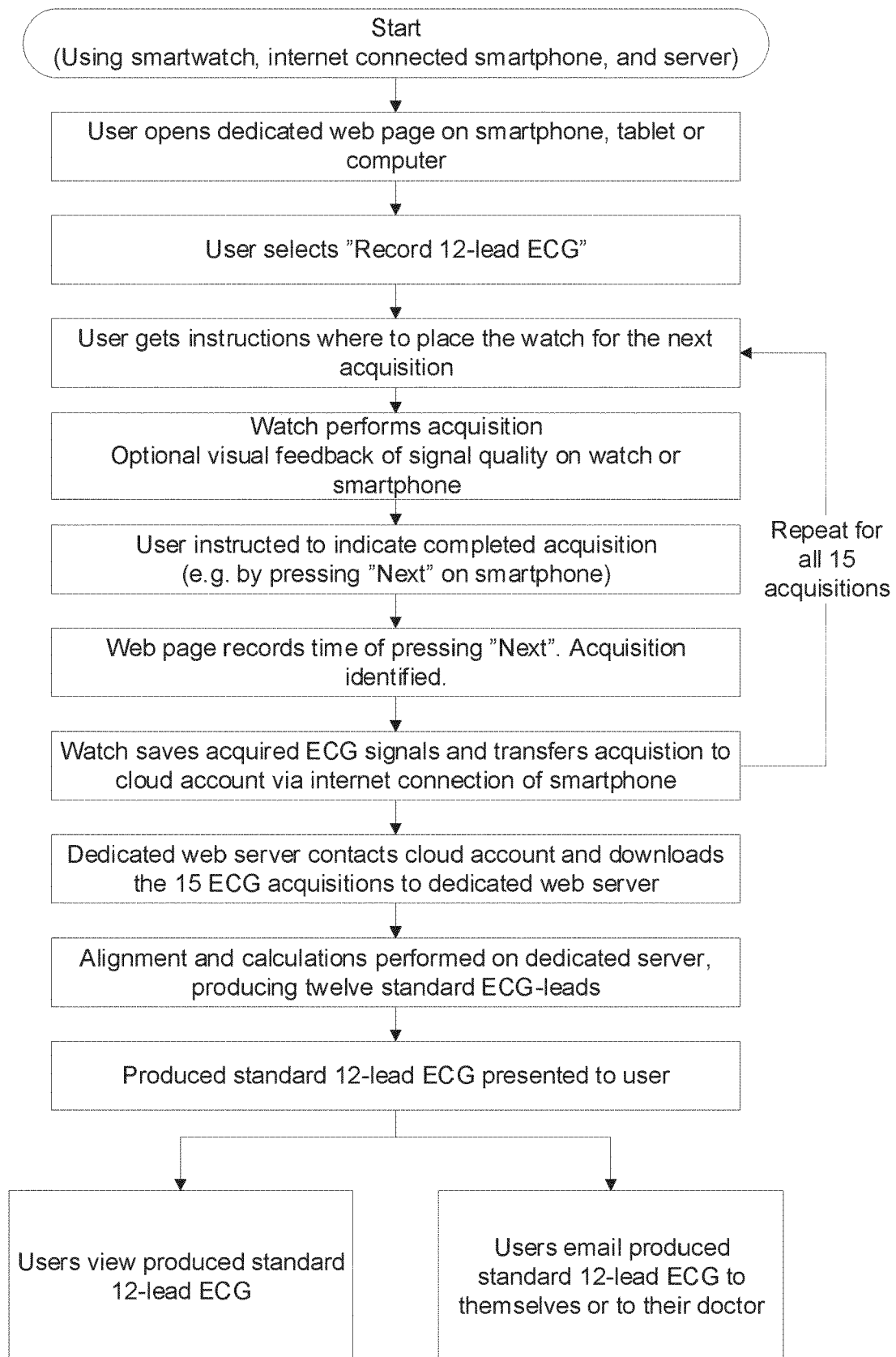
FIG. 15 is a flowchart illustrating acts of an embodiment of the invention.

FIG. 15 illustrates a flowchart including a sequence of acts for producing a 12-lead standard ECG according to another embodiment of the inventive concept, using a system 100 according to an embodiment of the inventive concept, and schematically illustrated in FIG. 16. In this embodiment, the acts are performed partly by a wearable or portable electronic device, here in the form of a smartwatch 10, and partly by one or more external devices. In the system example shown in FIG. 16, the system 100 further comprises a connected smartphone 20, a cloud server 30 or the like, and a dedicated server 40, communicating with each other as illustrated in FIG. 16. A separate computer 50 may also be comprised communicating with smartphone 20, cloud server 30, and dedicated server 40. The connection between the smartwatch and the smartphone 20 may typically be via Bluetooth, while the connection to and from the servers 40, 50 may be via internet. The "at least one processing unit" comprised in the system 100 may in this example include one or more processing units in the watch 10, the smartphone 20, the cloud server 30, and/or the dedicated server 40. As mentioned above, the acts of time-alignment and calculation may essentially be performed anywhere.

The acquisition sequence is similar to Example I in FIG. 14, except that the user initiates the acquisition by opening a dedicated app or web page on e.g. the smartphone 20. After selecting "Record 12-lead ECG" on the dedicated app or web page, the user receives instructions on where to place the smartwatch 10 for the first of the fifteen acquisitions. A 30 second long (or some other predetermined time period) acquisition of an ECG signal is performed, representing lead I. As in the previous example and as illustrated at reference numeral 21, the ECG signal quality may optionally be observed "live" during the acquisition on the smartphone 20, to give a visual feedback on the signal quality. Such visual feedback may also be provided on the display of the smartphone 10 as shown at reference numeral 11, or not at all. After the completion of acquisition for the lead, the user is instructed to give an input to indicate completion of acquisition of the first lead, for instance by again pressing a "Next" button on the webpage or app 20. The point in time is registered, and the registered time is associated with the most recent acquisition before the registered time. Thereby, each acquisition will be associated with a "label" so that the system will know which acquisition correspond to which one of the fifteen sequentially acquired leads. The web page or app records the time of pressing "Next", and the ECG acquisitions are subsequently identified by being that acquired immediately prior in time having pressed the "Next" button.

At the conclusion of either all or each of the acquisitions, the smartwatch 10 saves the ECG signals to the smartphone app, and the smartphone app transfers the ECG acquisitions to the Cloud server 30 via the internet connection of the smartphone 20.

At the conclusion of the final 15$^{th}$ acquisition, the dedicated web server 40, which may alternatively be a smartphone-based app, contacts the cloud server 30 and downloads the fifteen ECG acquisitions to the dedicated server 40, where the alignments and calculations are made according to the inventive concept. Thereafter, the produced 12-lead ECG similar to the ECG shown in FIG. 12 is presented to the user. As shown in FIG. 16, the produced 12-lead ECG may be sent to the smartphone 20 and/or to a computer 50 where the 12-lead ECG may be shown on a larger display as indicated at reference numeral 51. The user may view the ECG, or email it to themselves or their healthcare professional as a pdf for example.

In this example, if the user does not have access to the smartphone initially, the recording may still be performed using the smartwatch. The acquired leads will be transferred automatically to the smartphone next time the smartwatch and the smartphone are connected, and subsequently transferred to the cloud and ultimately used to calculate and display a standard 12-lead ECG.

Below are examples of embodiments of the systems and methods described herein.

Disclosed herein are methods and systems for determining or generating ECG(s) using a dual-electrode (e.g. single lead) device). The method may include obtaining a series of asynchronous (e.g., non-time aligned) measured leads. Each of the asynchronous measured leads may be acquired via two electrodes (e.g., single lead) of the device. The two electrodes (e.g., single lead) may be positioned at various positions of a patient's body during the acquisition of the series of asynchronous measured leads.

The method may include determining a respective time shift for one or more of the asynchronous measured leads. For example, a first lead may be determined by measuring a first potential (e.g., a voltage, voltage function, etc.) between two physical electrodes of the device (e.g. limb lead I). A second lead may be determined by measuring a second potential between the two physical electrodes of the device (e.g., limb lead II). A third lead may be determined by measuring a third potential between the two physical electrodes of the device (e.g., limb lead III). The first, second, and third leads may correspond to asynchronous measured leads (e.g., they may be obtained or measured serially in time). The first, second, and third leads may correspond to averaged waveforms of the asynchronous measured leads.

The method may include performing a time shift on one or more of the first lead or the second lead. For example, a time shift may be performed on one or more of the first lead or second lead in order to determine a time shift value that minimizes the difference between (a) the third lead (e.g., limb lead III) and (b) a difference between (i) the second lead (e.g., limb lead II), and (ii) the first lead (e.g., limb lead I). Once the time shift value has been determined that minimizes the difference between ((a) the third lead (e.g., limb lead III) and (b) a difference between (i) the second lead (e.g., limb lead II), and (ii) the first lead (e.g., limb lead I), the method may include determining a time-aligned version of the first lead, a time-aligned version of the second lead, and a time-aligned version of the third lead.

The time-aligned version of the first and second leads may be determined by applying the determined time shift value to one or more of the first or second leads. For example, the first lead may be used as a reference and the time shift value may be applied to the second lead. In another example, the second lead may be used as a reference and the time shift value may be applied to the first lead. In another example, part of the time shift value may be applied to each of the first and second leads to determine the time-aligned versions of the first and second leads. A time-aligned version of the third lead may be determined by taking a difference between the time-aligned version of the second lead and the time-aligned version of the first lead. In an example, the first, second, and third leads may correspond to asynchronously acquired limb leads (e.g., limb leads I-III). In an example, each of the first, second, and third leads may correspond to average beat waveforms that were determined based on asynchronous measurements from the device.

The method may further include using one or more of the time-aligned version of the first lead, the time-aligned version of the second lead, and/or the time-aligned version of the third lead to determine one or more virtual or augmented leads. For example, three augmented leads may be determined based on the time-aligned version of the first lead, the time-aligned version of the second lead, and the time-aligned version of the third lead. The three augmented leads may correspond to augmented limb leads aVR, aVL, and aVF. For example, the three augmented leads corresponding to augmented limb leads aVR, aVL, and aVF may be determined using the time-aligned version of the first lead, the time-aligned version of the second lead, and/or the time-aligned version of the third lead as limb leads I-III, respectively, in the formulas (4)-(6), above.

In an example, there may be 15 asynchronous leads that are determined or measured using the device. For example, the 15 asynchronous leads may include three asynchronous limb leads (e.g., limb leads six first asynchronous arm-referenced chest leads (e.g., CR1-CR6), and six second asynchronous arm-referenced chest leads (CL1-CL6). In an example, a respective average beat waveform may be determined for one or more or each of the 15 asynchronous leads. The averaging may be performed by aligning peaks within a respective asynchronous lead.

In an example, time alignment may be performed between one or more of the six first asynchronous arm-referenced chest leads (e.g., CR1-CR6) and one or more of the six second asynchronous arm-referenced chest leads (CL1-CL6) using the time-aligned versions of the three limb leads (e.g., the time-aligned version of the first lead, the time-aligned version of the second lead, and/or the time-aligned version of the third lead described above). For example, a time alignment may be performed between a first of the six first asynchronous arm-referenced chest leads (e.g., CR1), a first of the six second asynchronous arm-referenced chest leads (e.g., CL1), and the time-aligned version of the first lead.

For instance, the first of the six second asynchronous arm-referenced chest leads (e.g., CL1) may be used as an alignment reference for determining a time shift to apply to the first of the six first asynchronous arm-referenced chest leads (e.g., CR1) based on the time-aligned version of the first lead (e.g., time-aligned limb lead I). In another example, the first of the six first asynchronous arm-referenced chest leads (e.g., CR1) may be using as an alignment reference for determining a time shift to apply to the first of the six second asynchronous arm-referenced chest leads (e.g., CL1) based on the time-aligned version of the first lead.

As an example, a time-aligned version of the first of the six first asynchronous arm-referenced chest leads (e.g., CR1) may be determined by determining a time shift value that minimizes the difference between (a) the measured version of the first of the six second asynchronous arm-referenced chest leads (e.g., CL1) and (b) a difference between (i) the first of the six first asynchronous arm-referenced chest leads (e.g., CR1), and (ii) time-aligned version of the first lead (e.g., time-aligned limb lead I). The determined time shift that minimizes that difference can then be applied to the first of the six first asynchronous arm-referenced chest leads (e.g., CR1) in order to determine a time-aligned version of the first of the six first asynchronous arm-referenced chest leads (e.g., a time-aligned CR1). This process may then be repeated for the second of the six first asynchronous arm-referenced chest leads (e.g., CR2). In other words, a time-aligned version of the second of the six first asynchronous arm-referenced chest leads (e.g., CR2) may be determined by determining a time shift value that minimizes the difference between (a) the measured version of the second of the six second asynchronous arm-referenced chest leads (e.g., CL2) and (b) a difference between (i) the second of the six first asynchronous arm-referenced chest leads (e.g., CR2), and (ii) time-aligned version of the first lead (e.g., time-aligned limb lead I). Applying this determined time shift to the second of the six first asynchronous arm-referenced chest leads (e.g., CR2) can be used to determine a time-aligned version of the second of the six first asynchronous arm-referenced chest leads (e.g., a time aligned CR2). A similar time shift determination can be used to determined time-aligned versions of the third, fourth, fifth, and sixth of the six first asynchronous arm-referenced chest leads (e.g., time aligned CR3, time aligned CR4, time-aligned CR5, and time-aligned CR6, respectively).

The time-aligned first lead (e.g., time-aligned limb lead I), time-aligned second lead (e.g., time-aligned limb lead II), and six time-aligned first asynchronous arm-referenced chest leads (e.g., time-aligned CR1-6) can then be used to determine six standard precordial leads (e.g., precordial leads V1-V6). For example, the time-aligned first lead (e.g., time-aligned limb lead I), time-aligned second lead (e.g., time-aligned limb lead II), and six time-aligned first asynchronous arm-referenced chest leads (e.g., time-aligned CR1-6) can be used in formula (9), above, to determine the six standard precordial leads (e.g., precordial leads V1-V6).

Then, a standard 12-lead ECG can be obtained or formed by the time-aligned first lead (e.g., time-aligned limb lead I), time-aligned second lead (e.g., time-aligned limb lead II), time-aligned third lead (e.g., time-aligned limb lead III), the three determined augmented leads (e.g., aVR, aVL, and aVF), and the determined six standard precordial leads (e.g., precordial leads V1-V6).

It should be noted that the determinations or calculations may be performed by a processor and memory co-located with the device containing the electrodes (e.g., within a wearable such a smart watch), or by a processor in operable communication with the device containing the electrodes (e.g., a smart phone communicating with a smart watch, a server system in communication directly or indirectly with the smart watch, etc.). The processing steps may be performed by a single processor or divided between multiple processors. Additionally, the acquisition of the leads may be performed in any order. Although certain leads are used a time references in the examples described herein, which particular lead is used a time reference and which leads have time shifts applied may be varied based on design choice.

The invention claimed is:

1. A computer-implemented method for producing a standard 12-lead ECG formed by three standard limb leads I, II, III, three standard augmented limb leads aVR, aVL, aVF, and six standard precordial leads V1 to V6, from fifteen asynchronous, sequentially acquired leads, including three acquired limb leads I, II, and III, termed acquired leads I-III, and twelve acquired arm-referenced chest leads CR1-CR6 and CL1-CL6, termed acquired leads CR1-CR6 and CL1-CL6;

wherein, for integer i equal from 1 to 6, each pair of acquired leads CRi and CLi of acquired leads CR1-CR6 and CL1-CL6 represent voltage differences acquired between a right arm and a left arm, respectively, and a common chest position Ci associated with a corresponding standard precordial lead Vi, said method comprising:

creating time-aligned limb leads I, II and III, termed time-aligned leads I-III, from acquired leads I-III, by using the formula lead II−lead I=lead III;

calculating three time-aligned augmented limb leads aVR, aVL, and aVF from time-aligned leads I-III;

performing, for integer i equal from 1 to 6, one of (a) and (b):

(a) creating a time-aligned arm-referenced chest lead CRi, termed time-aligned CRi, by time-aligning acquired lead CRi with acquired lead I such that a calculated difference CRi−I, representing a calculated arm-referenced chest lead CLi, termed calculated lead CLi, has an optimal agreement with acquired lead CLi, (b) creating a time-aligned acquired arm-referenced chest lead CLi, termed time-aligned CLi, by time-aligning acquired lead CLi with acquired lead I such that a calculated sum CLi+I, representing a calculated arm-referenced chest lead CRi, termed calculated lead CRi, has an optimal agreement with acquired lead CRi;

and calculating, for integer i equal from 1 to 6, a time-aligned precordial lead Vi from time-aligned lead I, one of time-aligned lead II and time-aligned lead III, and one of time-aligned lead CRi and time-aligned lead CLi, for forming time-aligned precordial leads V1-V6;

wherein time-aligned leads I-III, time-aligned augmented leads limb leads aVR, aVL, and aVF, and time-aligned precordial leads V1-V6 together form a standard 12-lead ECG.

2. The method according to claim 1, further comprising averaging each acquired lead of the fifteen acquired leads for creating fifteen corresponding averaged beat waveforms, and using the averaged beat wave forms as acquired leads in the step of creating time-aligned leads I-III, and in step (a) and (b) of creating time-aligned leads CR1-CR6, and time-aligned leads CL1-CL6.

3. The method according to claim 1, wherein:
the time-aligning in step (a) is performed by iteratively shifting acquired lead CRi and acquired lead I in relation to each other to achieve said optimal agreement between said difference CRi−I and acquired lead CLi; and the time-aligning in step (b) is performed by iteratively shifting acquired lead CLi and acquired lead I in relation to each other to achieve said optimal agreement between said sum CLi+I and acquired lead CRi.

4. The method according to claim 1, wherein time-aligned lead I is created before performing step (a) or step (b), respectively, and the time-aligning in step (a) or (b), respectively, is performed using time-aligned lead I.

5. The method according to claim 1, wherein the act of creating time-aligned leads I-III comprises creating a first time-aligned lead and a second time-aligned lead of time-aligned leads I-III, by time-shifting associated first and second acquired leads of acquired leads I-III, using a third acquired lead of acquired leads I-III as reference; and calculating a remaining third time-aligned limb lead of time-aligned limb leads I-III from said first time-aligned lead and said second time-aligned lead.

6. The method according to claim 1, wherein said fifteen sequentially acquired leads are acquired using two electrodes only.

7. The method according to claim 6, wherein, for integer i equal from 1 to 6, acquired lead CRi and acquired CLi are measured sequentially, one directly after the other in any order, while keeping one of said two electrodes positioned at said common chest position Ci.

8. The method according to claim 1, further comprising averaging each time-aligned lead with an associated calculated version of the same lead, for creating an associated averaged time-aligned lead.

9. The method according to claim 1, wherein the method is performed using a single-lead wearable or portable electronic device comprising two electrodes; and wherein said fifteen sequentially acquired leads are acquired by sequentially changing positions of said two electrodes on the body of a subject.

10. A system for producing a standard 12-lead ECG formed by three standard limb leads I, II, III, three standard augmented limb leads aVR, aVL, aVF, and six standard precordial leads V1 to V6, the system comprising:
two electrodes;
at least one processing unit configured to perform the acts of:
sequentially acquiring fifteen ECG leads between the two electrodes, while the two electrodes are sequentially moved to different positions on a subject's body, including three acquired limb leads I, II, and III, termed acquired leads I-III, and twelve acquired arm-referenced chest leads CR1-CR6 and CL1-CL6, termed acquired leads CR1-CR6 and CL1-CL6, wherein, for integer i equal from 1 to 6, each pair of acquired leads CRi and CLi of acquired leads CR1-CR6 and CL1-CL6 represent voltage differences acquired between a right arm and a left arm, respectively, and a common chest position Ci associated with a corresponding standard precordial lead Vi;

creating three time-aligned limb leads I, II and III, termed time-aligned leads I-III, from acquired leads I-III, by using the formula lead II−lead I=lead III;

calculating three time-aligned augmented limb leads aVR, aVL, and aVF from time-aligned leads I-III;

for integer i equal from 1 to 6,
(a) creating a time-aligned arm-referenced chest lead CRi, termed time-aligned CRi, by time-aligning acquired lead CRi with acquired lead I such that a calculated difference CRi-I, representing a calculated arm-referenced chest lead CLi, has an optimal agreement with acquired lead CLi, or
(b) creating a time-aligned acquired arm-referenced chest lead CLi, termed time-aligned CLi, by time-aligning acquired lead CLi with acquired lead I such that a calculated sum CLi+I, representing a calculated arm-referenced chest lead CRi, has an optimal agreement with acquired lead CRi;
and calculating, for integer i equal from 1 to 6, a time-aligned precordial lead Vi from time-aligned lead I, one of time-aligned lead II and time-aligned lead III, and one of time-aligned lead CRi and time-aligned lead CLi, for forming time-aligned precordial leads V1-V6;

wherein time-aligned leads I-III, time-aligned augmented leads limb leads aVR, aVL, and aVF, and time-aligned precordial leads V1-V6 together form a standard 12-lead ECG.

11. The system according to claim 10, wherein the system is incorporated in a portable or wearable electronic device comprising said two electrodes and comprising said at least one processing unit configured to perform said acts.

12. The system according to claim 11, wherein the said electronic device is an electronic device, such as smartwatch, a smartphone or a dedicated ECG device.

13. The system according to claim 10, wherein the system is incorporated partly in a portable or wearable electronic device comprising said two electrodes, and partly in at least one external device, said electronic device and said at least one external device being configured to communicate with each other.

14. The system according to claim 13, wherein said at least one external device comprises at least one server.

15. A non-transitory computer-readable recording medium having recorded thereon a program comprising program code portions which when executed on one or more processing units are configured to perform the computer-implemented method according to claim 1.

16. The non-transitory computer-readable recording medium according to claim 15, wherein said program code portions when executed on the electronic device are further configured to control acquisition of the fifteen acquired leads.

* * * * *